(12) United States Patent
Coyle

(10) Patent No.: US 8,676,301 B2
(45) Date of Patent: Mar. 18, 2014

(54) GUIDE WIRE INCORPORATING A HANDLE

(75) Inventor: James A. Coyle, County Galway (IE)

(73) Assignee: Med Works Limited, Co Roscommon (IE)

( * ) Notice: Subject to any disclaimer, the term of this patent is extended or adjusted under 35 U.S.C. 154(b) by 150 days.

(21) Appl. No.: 13/182,549

(22) Filed: Jul. 14, 2011

(65) Prior Publication Data

US 2013/0018359 A1 Jan. 17, 2013

(51) Int. Cl.
*A61B 1/01* (2006.01)
*A61M 25/00* (2006.01)
*A61M 25/09* (2006.01)

(52) U.S. Cl.
USPC ............ 600/434; 600/585; 604/538; 606/108

(58) Field of Classification Search
USPC ................... 600/434, 585; 604/538; 606/108
See application file for complete search history.

(56) References Cited

U.S. PATENT DOCUMENTS

| | | | |
|---|---|---|---|
| 4,345,602 A * | 8/1982 | Yoshimura et al. | 604/23 |
| 4,747,831 A * | 5/1988 | Kulli | 604/110 |
| 5,117,839 A | 6/1992 | Dance | |
| 5,246,426 A * | 9/1993 | Lewis et al. | 604/168.01 |
| 5,325,868 A | 7/1994 | Kimmelstiel | |
| 5,334,187 A | 8/1994 | Fischell et al. | |
| 5,704,914 A * | 1/1998 | Stocking et al. | 604/164.07 |
| 5,725,534 A * | 3/1998 | Rasmussen | 606/108 |
| 5,755,695 A | 5/1998 | Erickson et al. | |
| 5,876,375 A | 3/1999 | Penny | |
| 5,938,623 A * | 8/1999 | Quiachon et al. | 600/585 |
| 6,264,630 B1 | 7/2001 | Mickley et al. | |
| 6,512,957 B1 | 1/2003 | Witte | |
| 6,752,800 B1 | 6/2004 | Winston et al. | |
| 6,949,104 B2 | 9/2005 | Griffis et al. | |
| 7,682,365 B2 | 3/2010 | Guinan | |
| 2003/0097080 A1* | 5/2003 | Esashi et al. | 600/585 |
| 2004/0039372 A1 | 2/2004 | Carmody | |
| 2004/0106852 A1 | 6/2004 | Windheuser et al. | |
| 2004/0181177 A1* | 9/2004 | Lee et al. | 600/585 |
| 2005/0154371 A1* | 7/2005 | Miyata et al. | 604/510 |
| 2005/0165355 A1* | 7/2005 | Fitzgerald | 604/164.08 |
| 2005/0177073 A1 | 8/2005 | Shiber | |
| 2006/0229496 A1 | 10/2006 | Windheuser et al. | |

(Continued)

FOREIGN PATENT DOCUMENTS

| | | |
|---|---|---|
| WO | 2007006055 A2 | 1/2007 |
| WO | 2012039906 A1 | 3/2012 |

OTHER PUBLICATIONS

European Patent Office, International Searching Authority, International Search Report and Written Opinion of the International Searching Authority mailed Nov. 14, 2012.

*Primary Examiner* — Sean Dougherty
(74) *Attorney, Agent, or Firm* — Nikolai & Mersereau, P.A.; C. G. Mersereau

(57) ABSTRACT

A guide wire incorporating a handle that incorporates a handle at the proximal end of said guide wire, the handle incorporating a guide wire actuator slidably disposed upon an actuator rail, the guide wire actuator being affixed to the proximal end of the guide wire and a guard rail contained within the actuator rail that prevents buckling of the proximal end of the guide wire. The handle can be connected to a catheter device amalgamating the guide wire and the catheter, allowing the catheter and guide wire to be operated simultaneously while also enabling the guide wire to be advanced or torqued independently of the catheter device.

21 Claims, 14 Drawing Sheets

(56) References Cited

U.S. PATENT DOCUMENTS

| | | |
|---|---|---|
| 2008/0077227 A1 | 3/2008 | Ouellette et al. |
| 2008/0264102 A1 | 10/2008 | Berra |
| 2010/0030113 A1 | 2/2010 | Morriss et al. |
| 2010/0030318 A1 | 2/2010 | Berra |
| 2010/0056910 A1 | 3/2010 | Yanuma |
| 2010/0094310 A1 | 4/2010 | Warring et al. |
| 2010/0210934 A1 | 8/2010 | Belson |
| 2011/0054487 A1* | 3/2011 | Farnan .................. 606/108 |

* cited by examiner

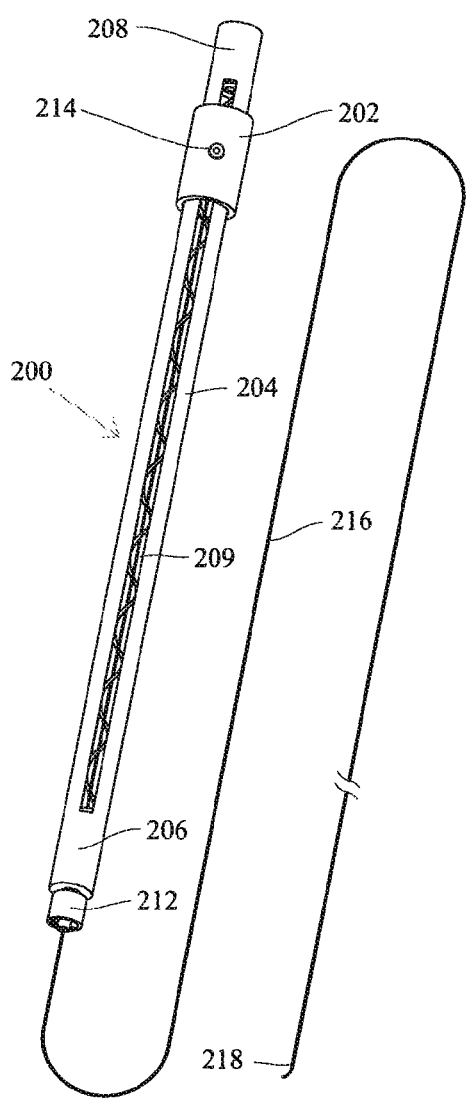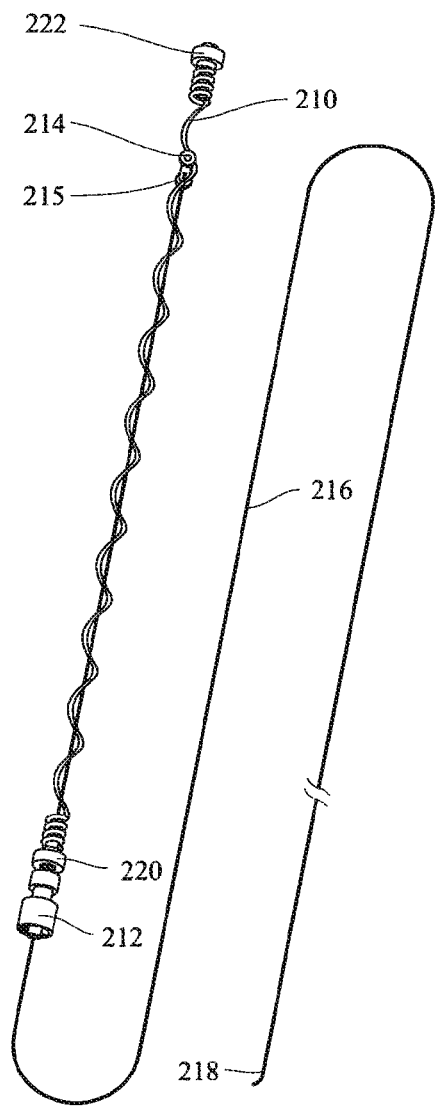
FIG. 2                    FIG. 3

GUIDE WIRE INCORPORATING A HANDLE

CROSS-REFERENCED TO RELATED APPLICATIONS

Not applicable

STATEMENT REGARDING FEDERALLY SPONSORED RESEARCH OR DEVELOPMENT

Not applicable

FIELD OF THE INVENTION

The present invention relates to a medical device. More specifically the invention relates to a guide wire that incorporates a handle that can be connected to a catheter device, conjoining the guide wire and the catheter device to enable the handle to advance the two devices simultaneously. The handle incorporates a guide wire actuator slidably disposed upon the handle that can be used to operate the guide wire independent of the catheter device.

BACKGROUND OF THE INVENTION

Medical device guide wires are used for a variety of purposes in the treatment of many minimally invasive procedures. Medical device guide wires are manufactured in a range of diameters including 0.014 inch, 0.018 inch, 0.025 inch, 0.032 inch, 0.035 inch and 0.038 inch and a range of lengths including 150 centimeters, 180 centimeters and 300 centimeters. Medical device guide wires are often used in a procedure to provide a pathway over which a therapeutic device such as a catheter is passed. Medical device guide wires are used in many areas of treatment including interventional cardiology, interventional radiology, interventional bronchospy, gastroenterology and urology for a variety of purposes including the placement of vena cava filters, cryotherapy, biliary drainage, angioplasty and stenting.

Catheters are inserted to various locations within a patient for a wide variety of purposes and medical procedures. For example only, one type of catheter is used in percutaneous catheter intervention (PCI) for the treatment of a vascular constriction termed a stenosis. In this instance, the catheter has a distally mounted balloon that can be placed, in a deflated condition, within the stenosis, and then inflated to dilate the narrowed lumen of the blood vessel. Such balloon dilation therapy is generally named percutaneous transluminal angioplasty (PTA). The designation PTCA, for percutaneous transluminal coronary angioplasty, is used when the treatment is more specifically employed in the vessels of the heart. PTCA is used to dilate restrictions in the coronary arteries that have become narrowed or occluded by a build-up of cholesterol fats or atherosclerotic plaque. The balloon at the distal end of the catheter is positioned within the stenosis and inflated causing the stenosis to widen.

The dilation of the occlusion, however, can form flaps, fissures and dissections, which may result in reclosure of the dilated vessel or even perforations in the vessel wall. Implantation of a stent can provide support for such flaps and dissections and thereby prevent reclosure of the vessel or provide a patch repair for a perforated vessel wall until corrective surgery can be performed. A stent is typically a cylindrically shaped device formed from wire(s) or a metal tube with segments of the tube removed. A stent is deployed in a body lumen from a radially compressed configuration into a radially expanded configuration that allows it to contact and support a body lumen. A stent may be implanted during an angioplasty procedure by using a balloon catheter with a radially compressed stent mounted onto the balloon of the catheter. The stent radially expands as the balloon is inflated, forcing the stent into contact with the body lumen, thereby forming a supporting relationship with the lumen walls. Alternatively, self-expanding stents may be deployed with a sheath-based delivery catheter. Deployment is effected after the stent has been introduced percutaneously, transported transluminally and positioned at a desired location by the delivery catheter. Typically, retraction of the sheath covering the radially compressed stent allows the self-expanding stent to deploy. In addition to angioplasty and stenting procedures, other therapeutic procedures often require use of a delivery catheter, such as drug delivery, embolic filters, occlusion devices, diagnostic devices and radiation treatment.

Typically, the placement of such therapeutic delivery catheters involves the use of a guide wire, which may be inserted into the patient's vasculature through the skin, and advanced to the location of the treatment site. The delivery catheter, which has a lumen adapted to receive the guide wire, then is advanced over the guide wire. Alternatively the guide wire and delivery catheter may be advanced together, with the guide wire protruding from the distal end of the delivery catheter. In either case, the guide wire serves to guide the delivery catheter to the location to be treated.

In cases where the lesion targeted for treatment is located distant from a convenient vascular access location, the therapeutic procedure usually starts with the introduction of a guiding catheter into the vascular system from an easily reachable site, such as through the femoral artery in the groin area or other locations in the arm or neck. The guiding catheter is advanced through the arterial system until its distal end is located near the stenosis that is targeted for treatment. During PTCA, for example, the distal end of the guiding catheter is typically inserted only into the ostium or origin of a coronary artery. A guide wire may then be advanced through a main lumen in the guiding catheter and manipulated into position across the stenosis.

Coronary guide wires are flexible and susceptible to buckling and kinking. The distal end of a coronary guide wire, for example, is typically more flexible than the proximal end of the coronary guide wire. During PTCA the distal end of the guide wire must be tracked through the aortic arch and into a coronary artery or a coronary artery side branch vessel. The proximal end of the guide wire is generally stiffer than the distal end of the guide wire to provide sufficient column support to enable advancing of the guide wire through the vasculature. The proximal end of the guide wire must however be flexible enough to enable the guide wire to track through any tortuosity that exists. In instances where the guide wire is advanced independent of the catheter device dexterity is required while advancing the guide wire through the main lumen of the guide catheter to ensure no buckling or kinking of the guide wire occurs. Typically the guide wire is advanced in incremental pushes whereby a physician advances the guide wire by holding the wire a short distance proximal from the proximal end of the guide catheter lumen and advances this segment of guide wire up to the proximal end of the guide catheter lumen. This process is repeated until the guide wire is positioned across the stenosis. In effect the guide wire is advanced through the vasculature with a series of incremental pushes. A torque handle device may be loaded onto the proximal end of the guide wire. The torque handle enables a physician to torque the guide wire to enable steering of the distal end of the guide wire for the purpose of steering the guide wire into a side branch vessel or to assist in crossing through a stenosis. Once the guide wire is in position the torque handle may be loosened and carefully removed while ensuring no longitudinal movement of the guide wire occurs. When the guide wire is in position the proximal end of the guide wire is typically rested on a surface extending from its entry point into the vasculature. During PTCA for example, when the access location is the femoral artery, the proximal end of the guide wire is often rested on a sheet that covers the patient's legs. This is not a very even surface so care must be taken to ensure that the proximal end of the guide wire remains stationary prior to advancing any therapeutic catheters over the guide wire or that the proximal end of the guide wire does not become kinked or damaged due to inadvertent manipulation.

A therapeutic delivery catheter such as a balloon catheter or a stent delivery system may then be advanced over the pre-positioned guide wire until the therapeutic element of the catheter is properly positioned at the treatment site. Three general types of catheters used during PTCA for example are: "over-the-wire" (OTW) catheters, "rapid exchange" (RX) catheters and "fixed wire" (FW) or "a balloon on a wire" catheters. An over-the-wire (OTW) catheter comprises a guide wire lumen that extends the entire length of the catheter. An OTW catheter typically has a "co-axial" catheter construction, wherein two hollow tubes are nested together. The inner tube can slidably receive guide wires and the annular luminal space formed between the inner and outer tubes is used for inflation/deflation fluid. OTW catheters have many advantages traceable to the presence of a full-length guide wire lumen such as good stiffness and pushability for readily advancing the catheter through tortuous vasculature and across tight stenoses. The full-length guide wire lumen is also available for transporting radiocontrast dye to the stenosed artery, for making pressure measurements, for infusing drugs and for other therapies. The full length guide wire lumen permits removal and replacement of a guide wire in an indwelling catheter, as may be required to alter the shape of the guide wire tip or if the guide wire becomes damaged.

In instances where a guide wire is first advanced into the vasculature and positioned across a stenosis followed by an OTW catheter, the distal end of the OTW catheter is loaded onto the proximal end of the pre-positioned guide wire and carefully advanced while the guide wire is held stationary distal to the distal end of the OTW catheter. When the proximal end of the guide wire exits from the proximal end of the OTW catheter the guide wire may be held at the proximal end to ensure that no movement of the guide wire occurs as the OTW catheter is advanced. For example, FIG. 1A depicts an illustration of a treatment procedure where OTW catheter 107 has been loaded onto the pre-positioned guide wire 103. FIG. 1B is an enlarged sectional view of the aortic arch and the coronary arteries and the distal ends of the guide wire and the guide catheter. Patient 100 is positioned on his/her back on operating table 101. Sheet 102 is positioned covering the legs and abdomen of patient 100. Guide catheter 105 has been inserted through femoral artery access location 109 and advanced through aorta 104 to aortic arch 110 and guide catheter tip 111 is positioned in ostium 113 of coronary vessel 112. The proximal end of guide catheter 105 rests on sheet 102. Tuohy buorst device 106 is connected to the proximal end of guide catheter 105. Guide wire 103 has been advanced through tuohy buorst adapter 106 and advanced through the lumen of guide catheter 105. Guide wire distal end 115 is positioned across stenosis 114. OTW catheter 107 has been loaded onto guide wire 103. Guide wire proximal end 108 has exited from the proximal end of OTW catheter 107.

In the illustration shown in FIG. 1A the proximal portion of guide wire 103 protruding from the patient must be longer than the length of OTW catheter 107 to enable guide wire 103 to be held when it exits from the proximal port of the guide wire lumen of OTW catheter 107 prior to the distal end of OTW catheter 107 entering into the vasculature. This is to facilitate changing the holding point of guide wire 103 from a point distal to OTW catheter 107 to a point proximal to OTW catheter 107 when guide wire 103 exits from the proximal end of the guide wire lumen of OTW catheter 107. As a consequence, the length of a guide wire required to advance an OTW catheter over a pre-positioned guide wire must be greater than the length of the OTW catheter plus the length of the segment of the guide wire pre-positioned within the vasculature. For example, an OTW PTCA catheter may typically be on the order of 145 centimeters long so that a guide wire used in conjunction with such a catheter may be on the order of 300 centimeters long. This is disadvantageous insofar as this length of guide wire protruding from the patient may be difficult to manage and may be susceptible to inadvertent movement or kinking. For example, when the access point is the femoral artery the proximal end of the guide wire is typically rested on the sheet covering the patient's legs. This is an uneven surface compared to a table top or the like so that care must be taken to ensure that the segment of guide wire protruding from the patient does not move upon this uneven surface or does not become kinked due to inadvertent manipulation of the unsupported guide wire segment.

Catheter designs have been developed that partially address the aforementioned shortcomings of OTW catheters. Rapid exchange (RX) catheters have a guide wire lumen that extends within only the distal portion of the catheter. Catheters of this type are formed so that the guide wire is located outside of the catheter except for the distal portion of the catheter that encompasses the guide wire lumen. The rapid exchange catheter's proximal exit port for the guide wire is typically located about 5 centimeters to 30 centimeters proximal to the catheter distal end. With an RX catheter the guide wire is typically inserted and positioned within the vasculature. The distal tip of the RX catheter is then loaded onto the proximal end of the pre-positioned guide wire while holding the guide wire at a location distal to the distal tip of the RX catheter to ensure that no movement of the pre-positioned guide wire occurs. Alternatively the tuohy buorst adapter may be tightened upon the pre-positioned guide wire to ensure no longitudinal movement occurs. The guide wire can be held at the proximal end when it exits from the proximal guide wire port of the RX catheter. Typically a guide wire of the order of 180 centimeters long is sufficient when used with a RX catheter as the segment of the pre-positioned 180 centimeter guide wire protruding from the patient is longer than the guide wire lumen of the RX catheter and enables the guide wire to be held proximal to the proximal guide wire port of the RX catheter before the distal tip of the RX catheter enters the vasculature.

A significantly shorter segment of guide wire protrudes from the patient when using a RX catheter and a guide wire of the order of 180 centimeters in length as opposed to an OTW catheter and a guide wire of the order of 300 centimeters in length. This shorter segment of guide wire protruding from the patient is more manageable than the segment of the longer guide wire protruding from the patient when used in conjunction with an OTW catheter. Nevertheless, the proximal segment of guide wire protruding from the patient must be rested on a typically uneven surface and care must be taken to ensure no inadvertent movement of the guide wire occurs or that the unsupported segment of guide wire protruding from the patient does not become kinked due to inadvertent manipulation.

Although an RX catheter system may avoid the requirement of using guide wires of the order of 300 centimeters in length, there are some noted difficulties with this type of catheter. Without a full length guide wire lumen, the proximal shaft of a RX catheter lacks an OTW catheter's coaxial relationship with the guide wire, which provides optimal transmission of force to push the distal end of the catheter through tight stenoses or/and tortuous blood vessels. When a RX catheter is advanced through a guide catheter over a guide wire only the distal portion of the RX catheter encapsulates the guide wire. The remaining proximal portion of the catheter runs alongside the guide wire within the guide catheter. This portion of the catheter lacks the coaxial relationship with the guide wire that exists along the full length of an OTW catheter being advanced under similar circumstances. As a result the proximal portion of a RX catheter is more susceptible to buckling within the guide catheter. Improvements to RX catheters have incorporated stiff metal proximal shafts and axial overlap between the stiff proximal shaft and the guide wire lumen to overcome the deficiencies discussed above. Nevertheless, such RX catheters still are not optimal in terms of transmission of force to push the distal end of the catheter.

Another difficulty associated with RX catheters is that it is not possible to exchange guide wires in an in-dwelling RX catheter as can be done with an OTW catheter. Since the proximal guide wire port of an in-dwelling RX catheter is contained within the lumen of a guide catheter it is not possible to retract the guide wire from the guide wire lumen of the RX catheter and subsequently re-advance the guide wire into the proximal guide wire port of a RX catheter as may be required to reshape the tip of the guide wire or to replace the existing guide wire due to, for example, damage to the tip of the guide wire.

Another difficulty associated with RX catheters is encountered at the proximal end of the catheter system. There the RX catheter and the guide wire extend from the guiding catheter side by side, making it awkward to seal the system against blood loss during manipulation of the guide wire and/or the RX catheter. A "Tuohy Buorst" fitting is typically used to form a seal at the proximal end of the guiding catheter to prevent blood loss from the system during manipulation of the guide wire and/or the RX catheter within the vasculature. The "Tuohy Buorst" fitting typically contains a manually adjustable, elastomeric, cylindrical gasket with a round center hole. Adjustment of the elastomeric gasket in the form of longitudinal compression causes the center hole to reduce in diameter and hence form a seal around the indwelling device(s) to prevent blood loss from the patient. This arrangement works well for an OTW catheter because only a cylindrical shaft extends from the guiding catheter since the guide wire is encapsulated within the cylindrical shaft arrangement. However, with a RX device, since the guide wire runs alongside the proximal shaft of the RX catheter, it is more difficult for the "Tuohy Buorst" device to seal against blood loss.

A RX catheter does not contain a full length guide wire lumen, so a physician cannot use the guide wire lumen for other purposes such as injection of contrast dye distal to the stenosis, infusing of therapeutic drugs, or for pressure measurements.

Another type of catheter device known as a "fixed wire" (FW) or "a balloon on a wire" catheter typically incorporates a non-removable guide wire into the design of the catheter. FW catheters typically have a short segment of guide wire protruding from the distal end of the catheter. In use a FW catheter may be advanced through a guide catheter without the requirement of having to advance a separate guide wire because the guide wire is an integral part of the FW device. The distal segment of guide wire is typically of the order of 1-2 centimeters in length and protrudes distally from the distal end of the balloon of such catheters. In addition there is not any segment of guide wire protruding proximally from the device that may be subjected to inadvertent movement or kinking. When a FW catheter is advanced through the vasculature the distal segment of guide wire assists in guiding the catheter through the vasculature. The tip segment may also be shaped into a bend configuration to assist in crossing through a stenosis or selecting a side branch vessel. Torqueing the proximal end of such a FW catheter will result in the distal segment rotating to assist steering of the device through the vasculature to enable crossing through a stenosis or selection of a side branch vessel. However, by the nature of the design of a FW catheter, the distal end of the catheter is typically already within the vessel when the guide wire tip section is being negotiated across a stenosis or being negotiated into a side branch vessel. In such instances the balloon or stent of the FW catheter may be advanced, retracted or rotated against the treatment vessel wall during manipulation of the distal end of the guide wire to the treatment site, increasing the likelihood of vessel trauma. No such concern exists when using OTW or RX catheters as the guide wire can first be negotiated into position prior to advancing the catheter itself.

Another difficulty with FW catheters is encountered if a dissection occurs within the vessel during inflation of a balloon. A dissection of the vessel typically involves some perforation or tearing of the vessel wall in proximity of the balloon inflation or other therapeutic intervention. In such instances it may be pertinent to deploy a stent within the dissected segment of vessel and it is critical to ensure the guide wire remains positioned across the damaged section of vessel because it may not be possible to re-cross a guide wire through the dissected segment of vessel to enable advancing a stent delivery catheter to the dissected segment of vessel. If a dissection occurs when using a FW catheter, with a non-removable guide wire, it will not be possible to leave the guide wire in position and remove the FW catheter prior to stenting as the guide wire is an integral part of the catheter.

It is therefore desirable to have a guide wire system that enables conjoining of a guide wire and an OTW catheter device so that the conjoined devices incorporate the advantages of a FW catheter but not the disadvantages of a FW catheter. It is also desirable for the conjoined devices to incorporate the benefits and advantages of OTW catheters and RX catheters but not the disadvantages. It is also desirable to have a guide wire system that enables coupling of a guide wire and a catheter based device for the treatment of many different medical device procedures in areas such as interventional radiology, interventional bronchoscopy, gastroenterology, urology and other areas of treatment.

SUMMARY OF THE INVENTION

The present invention is a guide wire incorporating a handle that encapsulates the proximal end of the guide wire. The handle may be connected to a catheter to conjoin the two devices, to enable the conjoined devices to be operated together, or to be operated independently of each other. A guide wire actuator slidably disposed upon the handle is attached to the proximal end of the guide wire and may be used to advance, retract or rotate the guide wire independent of the conjoined catheter.

In one embodiment the guide wire handle includes a tubular elongate housing that has a distal end and a proximal end, a lumen extending from the distal end towards the proximal end for a majority of the length of the housing and at least one longitudinal slot along a majority of the length of the tubular housing. A catheter connector disposed within the distal end of the housing can rotate independently of the housing and can be used to connect the handle to a catheter.

A guard rail is disposed within the housing and serves to encapsulate the proximal segment of guide wire, thus preventing the possibility of the guide wire buckling through the longitudinal slot in the housing when the guide wire actuator is advanced, retracted or rotated. The guard rail is comprised of a rigid material shaped into an elongate helix formation and is housed within the tubular housing so that it may rotate freely but may not undergo axial displacement. The coils of the guard rail prevent the guide wire buckling through the longitudinal slot in the housing during guide wire manipulation. The guard rail will rotate when the guide wire actuator slides distally or proximally upon the tubular housing, allowing transverse access through the longitudinal slot to the inner lumen of the housing along the length of the longitudinal slot.

In another embodiment of the invention the guide wire may be detached from the guide wire actuator and removed from the device. This allows for removal of the guide wire from the conjoined devices. Other embodiments of the invention detail alternate designs of the guard rail and the tubular housing that encapsulates the guard rail.

A method for treating a vascular condition in accordance with another embodiment of the present invention involves providing a guide wire incorporating a handle and attaching it to an OTW catheter to conjoin the OTW catheter and the guide wire; positioning the guide wire actuator to expose a short distal segment of guide wire or to retract the guide wire distal end completely within the guide wire lumen of the OTW catheter, advancing the conjoined catheter and guide wire through an in-dwelling guide catheter device until the distal end of the OTW catheter is near the distal end of the guide catheter but still encapsulated within the guide catheter lumen; actuating the guide wire actuator while maintaining the handle stationary to advance the guide wire through the treatment vessel and positioning the distal end of the guide wire at the treatment site and advancing the handle device while holding the guide wire actuator stationary to advance the OTW catheter to the treatment site while maintaining the guide wire position stationary.

BRIEF DESCRIPTION OF THE DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the relevant art to make and use the invention. The drawings are not to scale.

FIG. 2 is a perspective view of a guide wire incorporating a handle in accordance with one embodiment of the invention;

FIG. 3 shows the embodiment of FIG. 2 with the guide wire actuator and the actuator rail omitted to clearly show the inner mechanisms they would otherwise obscure;

DETAILED DESCRIPTION

Specific embodiments of the present invention are now described with reference to the figures, wherein like reference numbers indicate identical or functionally similar elements. The following detailed description is merely exemplary in nature and is not intended to limit the invention or the application and uses of the invention. Although the description of the invention is in the context of treatment of blood vessels such as the coronary, carotid or renal arteries, the invention may also be used in any other body passageways where the treatment methodology comprises the use of a guide wire and a catheter based device that contains a guide wire lumen along the full length of the catheter based device. For example, the guide wire system of the invention could be used to assist in the placement of guide catheters, or the like, in addition to its use with OTW catheters. Thus any catheter system that is compatible with the guide wire handle system of the present invention could be combined advantageously. Furthermore, there is no intention to be bound by any expressed or implied theory presented in the preceding technical field, background, brief summary or the following detailed description.

Figure 1A:
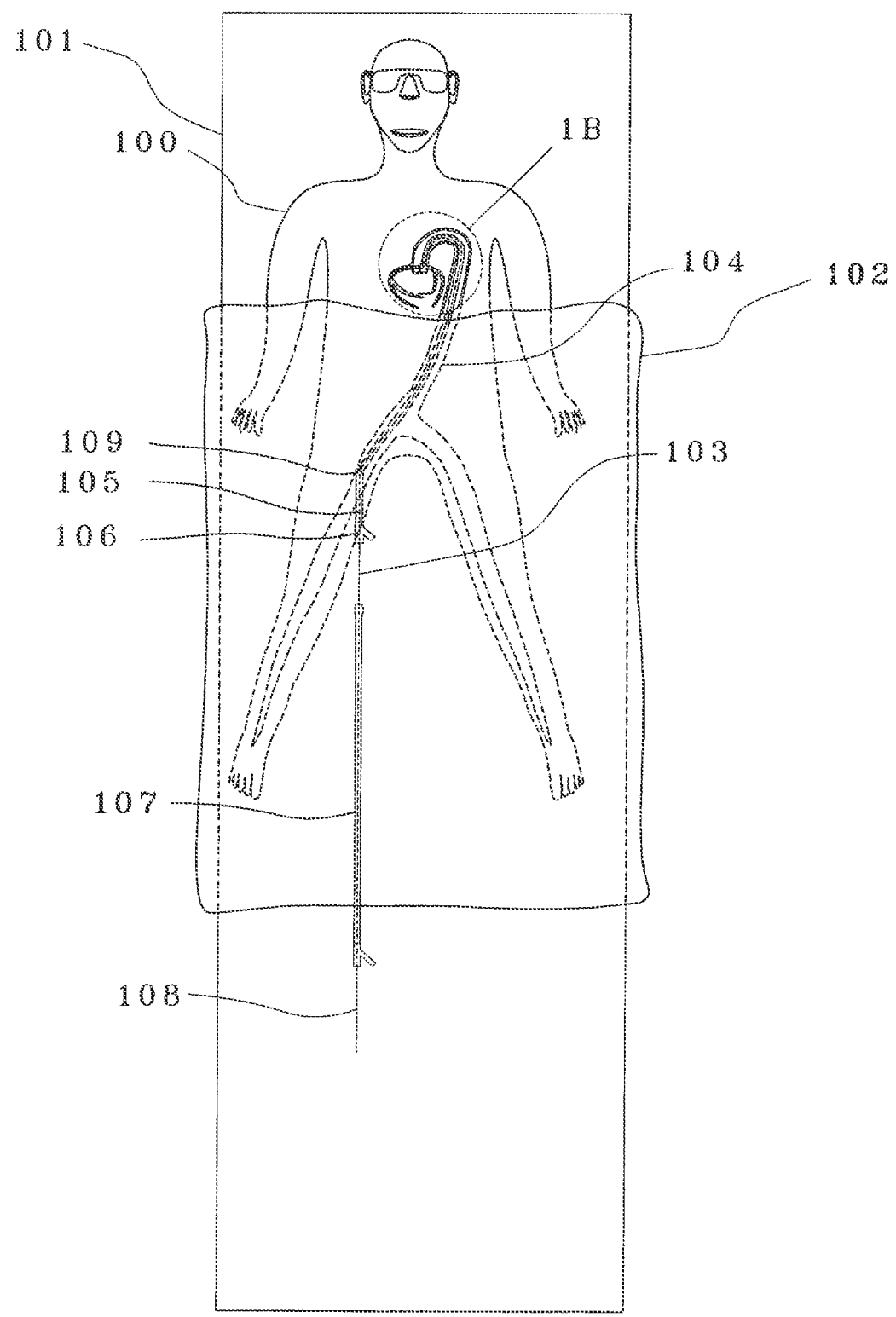
FIG. 1A is a prior art illustration of a patient undergoing a PTCA procedure performed using an OTW catheter device.
Figure 1B:
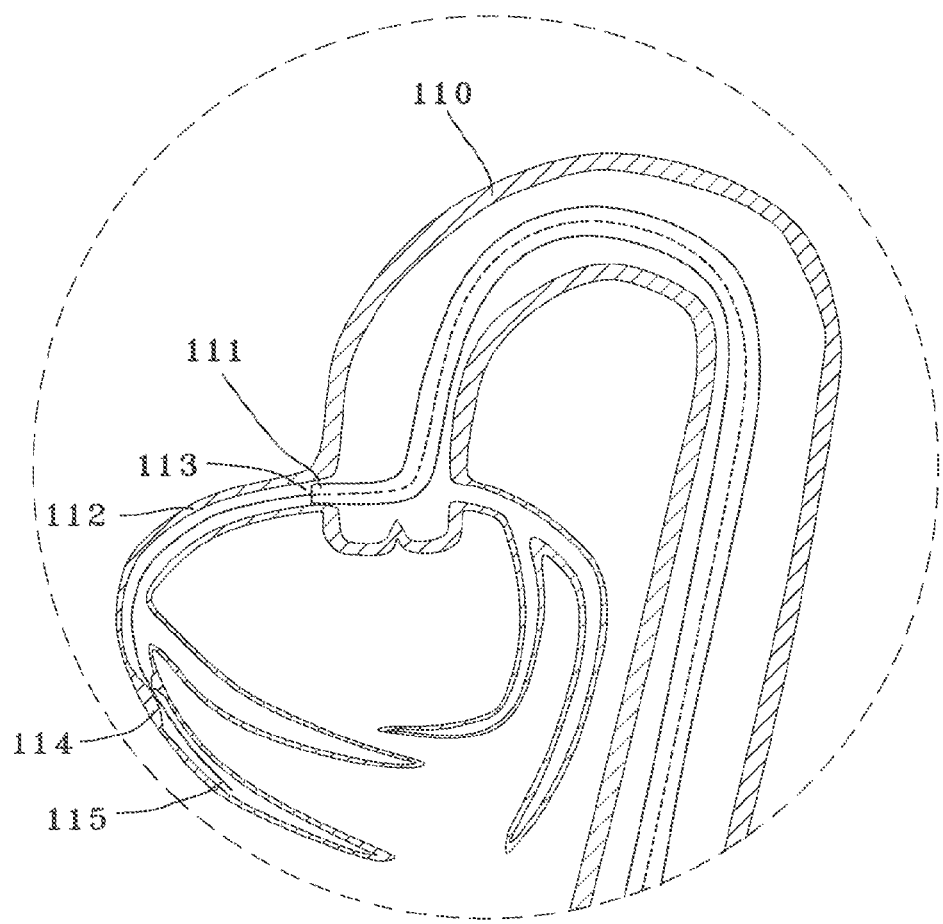
FIG. 1B is a prior art enlarged sectional view of the area circled and labeled 1B in FIG. 1A.
Figure 4A:
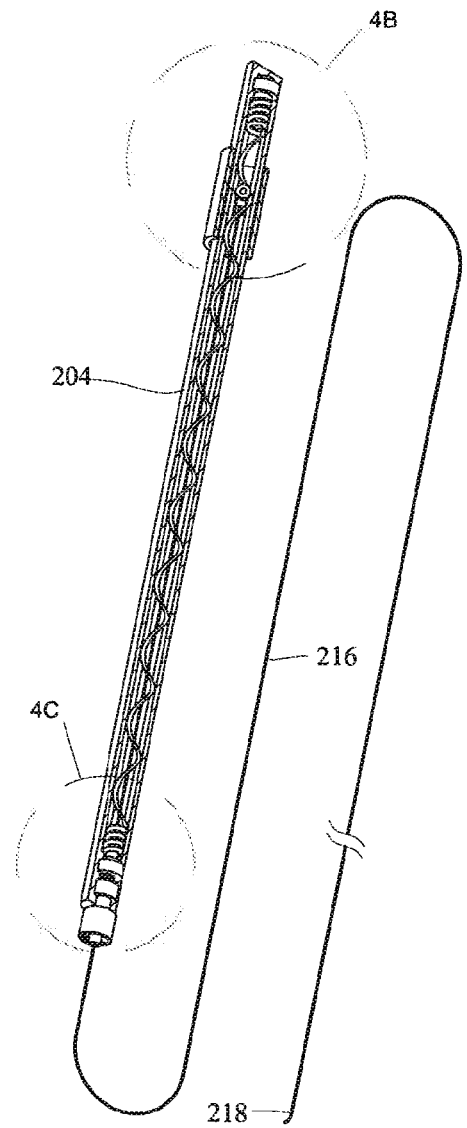
FIG. 4A is a perspective sectional view of the embodiment shown in FIG. 2.
Figure 4B:
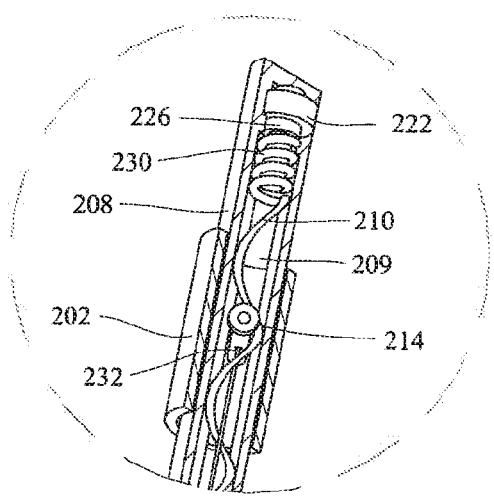
FIG. 4B is an enlarged view of the area circled and labeled 4B in FIG. 4A.
Figure 4C:
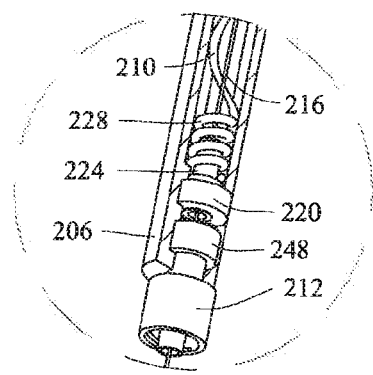
FIG. 4C is an enlarged view of the area circled and labeled 4C in FIG. 4A.

FIG. 2 shows a perspective view of guide wire incorporating a handle 200 in accordance with one embodiment of the invention. FIG. 3 shows the same perspective view of FIG. 2 with guide wire actuator 202 and actuator rail 204 omitted to clearly show the inner mechanisms they would otherwise obscure. FIG. 4A is a perspective sectional view of the embodiment shown in FIG. 2. FIG. 4B and FIG. 4C are enlarged views from FIG. 4A.

Guide wire incorporating a handle 200 comprises guide wire actuator 202 attached to guide wire 216 at guide wire proximal end 232, guide wire actuator 202 slidably disposed upon actuator rail 204 and guard rail 210 mounted within actuator rail 204. Actuator rail 204 is a generally tubular shaped component with an inner lumen that runs along a majority of its length. Actuator rail 204 incorporates catheter connector 212 and longitudinal slots 209 that enables access from outside actuator rail 204 to the inner lumen of actuator rail 204. Guard rail 210 prevents the proximal segment of guide wire 216 disposed within actuator rail 204 from buckling out through longitudinal slots 209 when guide wire actuator 202 is advanced along actuator rail 204 or when guide wire actuator 202 is rotated. Guide wire incorporating a handle 200 can be attached to an OTW catheter to conjoin guide wire 216 and an OTW catheter.

Guide wire distal end 218 can be inserted into the proximal guide wire port of an OTW catheter and advanced so that actuator rail 204 can be attached to the proximal end of the OTW catheter by means of catheter connector 212 disposed within actuator rail distal end 206.

Figure 5A:
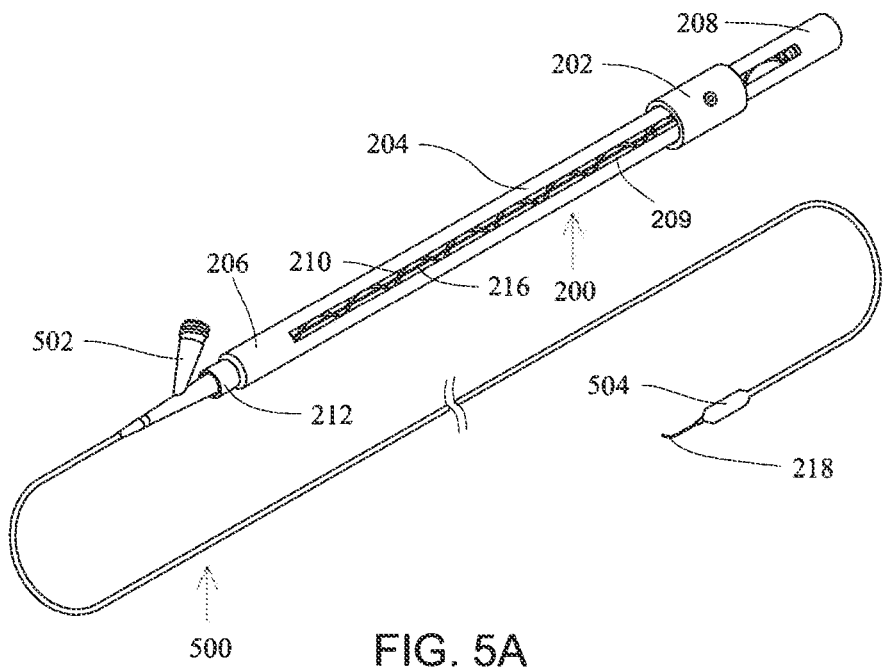
FIG. 5A is a perspective view of the embodiment shown in FIG. 2 conjoined with an OTW catheter device with the guide wire actuator positioned towards the proximal end of the actuator rail.
Figure 5B:
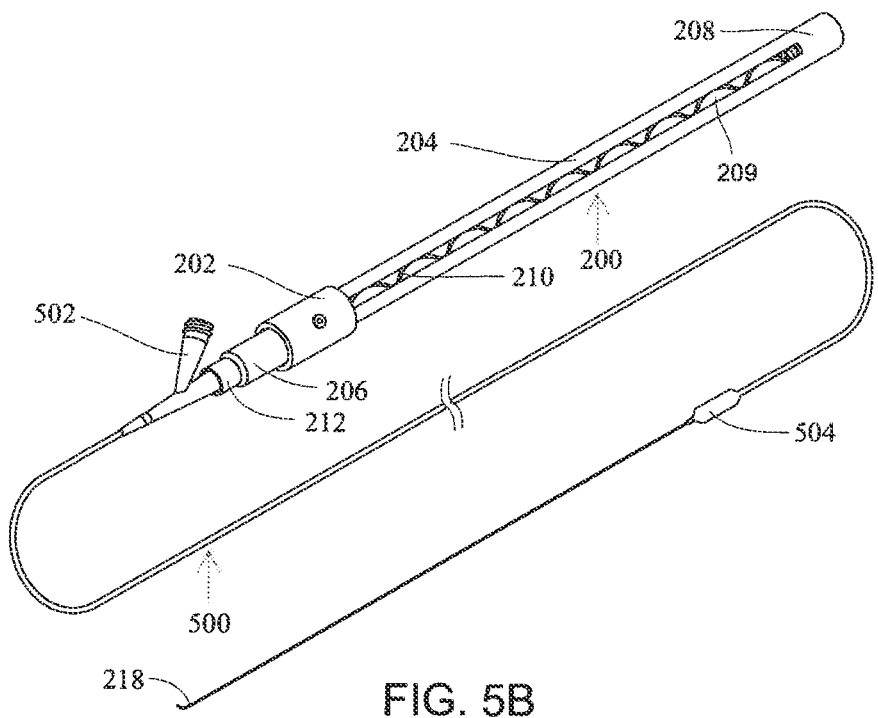
FIG. 5B is the same perspective view shown in FIG. 5A with the guide wire actuator positioned at the distal end of the actuator rail.

FIG. 5A is a perspective view of guide wire incorporating a handle 200 conjoined with OTW catheter 500. Catheter connector 212 is attached to the guide wire port of luer of OTW catheter 502 by means of interacting threaded portions of luer of OTW catheter 502 and catheter connector 212. Guide wire actuator 202 is positioned towards actuator rail proximal end 208. FIG. 5B is the same perspective view shown in FIG. 5A with guide wire actuator 202 positioned towards actuator rail distal end 206.

Guide wire actuator 202 can slide proximally upon actuator rail 204 to completely encapsulate guide wire distal end 218 within the guide wire lumen of OTW catheter 500 or guide wire actuator 202 can slide distally upon actuator rail 204 to expose a distal portion of guide wire 216 through the distal guide wire port of OTW catheter 500. Actuator 202 may be rotated to rotate guide wire 216 independent of OTW catheter 500. The proximal end of guide wire 216 remains contained within guard rail 210 housed within actuator rail 204. When guide wire actuator 202 slides distally or proximally upon actuator rail 204, guide wire holding pin 214, engages guard rail 210 so that guard rail 210 may rotate during movement of guide wire actuator 202, enabling guide wire holding pin 214 to remain in communication with inner lumen of actuator rail 204 along the length of longitudinal slots 209. In the embodiment shown in FIGS. 2, 3, 4A, 4B & 4C, guard rail 210 is mounted within actuator rail 204 by means of distal and proximal guard rail bearings, 220, 222, respectively, and distal and proximal guard rail connectors, 224, 226, respectively. Guard rail 210 is aligned within actuator rail 204 and may not undergo any axial displacement or misalignment within actuator rail 204. Distal and proximal guard rail bearings, 220, 222, ensure guard rail 210 may rotate with a minimum of friction.

Actuator rail 204 has distal and proximal ends, 206, 208, respectively, as shown in FIG. 2. Actuator rail 204 is a generally rigid, tubular shaped component with an inner lumen that extends from actuator rail distal end 206 towards actuator rail proximal end 208. Actuator rail 204 incorporates two longitudinal slots 209 that extend along a majority of the length of actuator rail 204. The inner surface of actuator rail 204 incorporates housings that facilitate secure disposal of distal and proximal guard rail bearings, 220, 222, respectively, and catheter connector 212 as shown in FIGS. 4A, 4B & 4C. Distal and proximal guard rail bearings, 220, 222, respectively, and catheter connector 212 reside securely disposed within actuator rail 204 without the risk of displacement or misalignment from these locations. Catheter connector 212 can rotate independent of actuator rail 204. Catheter connector 212 contains a threaded portion that can be securely connected to the threaded portion of the proximal guide wire port of an OTW catheter system.

Actuator rail 204 serves as a rail mechanism for guide wire actuator 202, enabling guide wire actuator 202 to slide in a proximal or distal direction for the length of longitudinal slots 209. Actuator rail 204 serves as the main body of guide wire incorporating a handle 200 and as a gripping member that may be used to advance the conjoined catheter and guide wire through the vasculature. Actuator rail 204 also serves to house guard rail 210 and the proximal end of guide wire 216 preventing the possibility of inadvertent bending or kinking of the proximal end of guide wire 216.

Actuator rail 204 may be molded from a suitable rigid plastic material such as nylon or nylon based co-polymers or from any suitable molding material. Alternatively actuator rail 204 may be made of a suitable metal material such as stainless steel or actuator rail 204 may comprise both metal and plastic components. Alternatively actuator rail 204 may be formed from machined components whereby the functionality of the machined components satisfies the functionality of the previously described molded component(s). For ease in manufacturing actuator rail 204 may be comprised of molded parts that snap-fit together to form the final configuration. Actuator rail 204 is generally cylinder shaped in the embodiment shown in FIG. 2 but may also incorporate any geometric configuration that enables the functionality previously described.

Guide wire actuator 202 is formed to be a slide fit upon actuator rail 204 and guide wire holding pin 214 projects into the inner lumen of actuator rail 204 through longitudinal slots 209 and is attached to guide wire proximal end 232. Guide wire holding pin 214 acts as a stop within longitudinal slots 209 preventing guide wire actuator 202 from sliding past the distal or proximal ends of longitudinal slots 209. Guide wire holding pin 214 ensures that rotation of guide wire actuator 202 about the longitudinal axis of actuator rail 204 results in rotation of actuator rail 204. When guide wire actuator 202 is advanced or retracted upon actuator rail 204, guide wire holding pin 214 travels within longitudinal slots 209 and advances or retracts guide wire 216 relative to actuator rail 204. Guide wire holding pin 214 may be attached to guide wire proximal end 232 using adhesive bonding, laser welding, uv curable bonds, mechanical attachment or any other means known to persons skilled in the art. Guide wire holding pin 214 is held in position within guide wire actuator 202 by means of holding screw 215 that threads into one end of guide wire holding pin 214.

Guide wire actuator 202 may be molded from a suitable rigid plastic material such as medical grade polycarbonate, polyvinyl chloride, acrylic, acrylonitrile butadiene styrene (ABS), nylon, nylon based co-polymers or other rigid biocompatible materials, or from any suitable molding material. Alternatively guide wire actuator 202 may be made of a suitable metal material such as stainless steel or guide wire actuator 202 may comprise both metal and plastic components. Alternatively guide wire actuator 202 may be formed from machined components whereby the functionality of the machined components satisfies the functionality of the previously described molded component(s). For ease in manufacturing guide wire actuator 202 may be comprised of molded parts that snap-fit together to form the final configuration.

Figure 6:
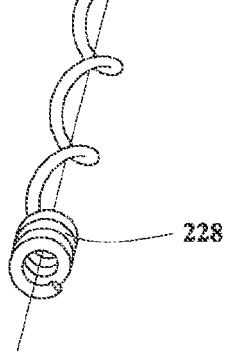
FIG. 6 is a perspective view of the guard rail of the embodiment shown in FIG. 2.

Guard rail 210 is a generally rigid structure formed from wire material wound about longitudinal axis 234 into a helix type formation as shown in FIG. 6. Guard rail distal and proximal segments, 228, 230, respectively are of the order of 1 centimeter in length and adjacent revolutions about longitudinal axis 234 are spaced very closely together or are in contact with each other. Guard rail distal and proximal segments, 228, 230, respectively, are so formed to form a cylindrical type lumen about longitudinal axis 234 of sufficient diameter, to allow for distal and proximal guard rail connectors, 224, 226, respectively, to be inserted into the cylindrical lumens formed and be a push fit within.

Distal and proximal guard rail connectors, 224, 226, respectively, are seated within the inner bore of distal and proximal guard rail bearings, 220, 222, respectively, to align guard rail 210 within actuator rail 204 so that guard rail 210 may under go rotation but may not under go axial displacement or misalignment within actuator rail 204. Distal and proximal guard rail bearings, 220, 222, respectively, serve to ensure guard rail 210 can rotate with a minimum of friction. The mid section of guard rail 210 is of the order of 25 centimeters in length in the embodiment shown in FIG. 6 and is comprised of 10 revolutions of wire about longitudinal axis 234 defining a helical path. The proximal segment of guide wire 216 is encapsulated within the helical formation of the mid section of guard rail 210.

Guide wire holding pin 214 of guide wire actuator 202 projects inwards through longitudinal slots 209 between adjacent revolutions of the helical formation of the mid section of guard rail 210 and can travel along longitudinal slots 209 and remains in communication with guide wire proximal end 232 encapsulated within guard rail 210.

Each revolution of the helical formation of the mid section of guard rail 210 provides a barrier between the proximal segment of guide wire 216 and longitudinal slots 209 preventing the proximal segment of guide wire 216 from buckling out through longitudinal slots 209. Adjacent revolutions of the helical formation of the mid section of guard rail 210 ensure that the longest length of unsupported guide wire 216 encapsulated within guard rail 210 is equal to the pitch of the helical formation of the mid section of guard rail 210. In the embodiment of FIGS. 2 & 3 the pitch of the helical formation of the mid section of guard rail 210 is of the order of 1 inch. This length of guide wire is not as susceptible to buckling when being advanced compared to a much longer length of guide wire. During actuator 204 advancing, guide wire holding pin 214 contacts guard rail 210 and causes guard rail 210 to rotate. The rotation of guard rail 210 allows guide wire holding pin 214 to travel along longitudinal slots 209 so that successive revolutions of mid section of guard rail 210 that traverse the path of guide wire holding pin 214 will be rotated out of the path of guide wire holding pin 214 allowing guide wire holding pin 214 to travel along the path of longitudinal slots 209 in communication with inner lumen of actuator rail 204.

In the embodiment shown in FIG. 6, the inner diameter of guard rail 210 is of the order of 3-7 millimeters and the outer diameter is of the order of 7-14 millimeters. In other embodiments, the different segments of guard rail 210 may have different inner or outer diameters. In addition, the pitch of guard rail 210 may be different than that shown in FIG. 6 and could contain a single pitch helix along the full length of guard rail 210 or could contain any other combination of pitches not illustrated in FIG. 6. In the embodiment shown in FIG. 6, the length of the mid section of guard rail 210 is of the order of 25 centimeters allowing guide wire actuator 202 to travel upon actuator rail 204 for a similar distance. The length of guard rail 210 could be significantly shorter or longer.

Guard rail 210 may be formed from any material that can be formed into a helix type shape, including stainless steel, spring wire, piano wire and nitinol. In the embodiment shown in FIG. 6, guard rail 210 is formed from stainless steel wire with a circular cross section and a diameter of the order of 2-3 millimeters although a wire of different diameter and/or different cross section could be used. The diameter of the forming wire is sufficient to form a helix with sufficient rigidity to allow guide wire holding pin 214 to rotate guard rail 210 mounted within actuator rail 204 without causing any bending of guard rail 210. Guard rail 210 is coupled to distal and proximal guard rail bearings, 220, 222, respectively by means of distal and proximal guard rail connectors, 224, 226, respectively.

Figure 7:
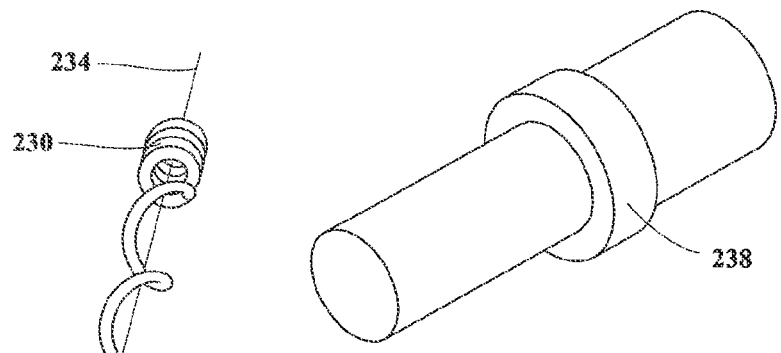
FIG. 7 is a perspective view of the proximal guard rail connector of the embodiment shown in FIG. 2.

Proximal guard rail connector 226 may include different diameter segments as shown in FIG. 7. Proximal guard rail connector 226 may be formed with suitable diameter segments that enable coupling of guard rail proximal segment 230 with proximal guard rail bearing 222. Proximal guard rail connector 226 may be a push or slide fit within guard rail proximal segment 230 and also be a push or slide fit within the bore of proximal guard rail bearing 222. Proximal guard rail connector 226 may include spacer element 238 to ensure that guard rail proximal segment 230 does not contact the outer ring of proximal guard rail bearing 222 and thus cause undesirable frictional forces that serve to resist rotation of guard rail 210.

Figure 8:
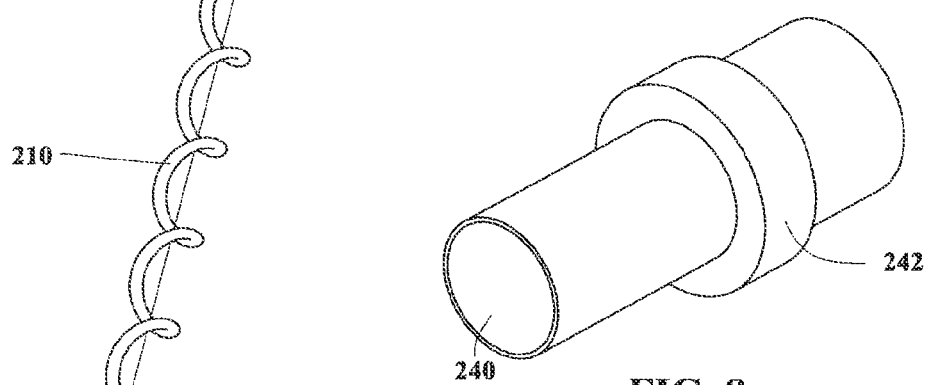
FIG. 8 is a perspective view of the distal guard rail connector of the embodiment shown in FIG. 2.

Distal guard rail connector 224 may include different diameter segments as shown in FIG. 8. Distal guard rail connector 224 may be formed with suitable diameter segments that enable coupling of guard rail distal segment 228 with distal guard rail bearing 220. Distal guard rail connector 224 has central lumen 240 throughout the length of the connector to enable guide wire 216 to pass freely through. Distal guard rail connector 224 may be a push or slide fit within guard rail distal segment 228 and a push or slide fit within the bore of distal guard rail bearing 220.

Distal guard rail connector 224 may include spacer element 242 to ensure that guard rail distal segment 228 does not contact the outer ring of distal guard rail bearing 220 and thus cause undesirable frictional forces that serve to resist rotation of guard rail 210. Distal and proximal guard rail connectors, 224, 226, respectively, may be formed of medical grade polycarbonate, polyvinyl chloride, acrylic, acrylonitrile butadiene styrene (ABS), nylon or other rigid biocompatible material. Distal and proximal guard rail connectors, 224, 226, respectively, may be formed using a molding process or may be machined using other processes known to those skilled in the art.

Figure 9:
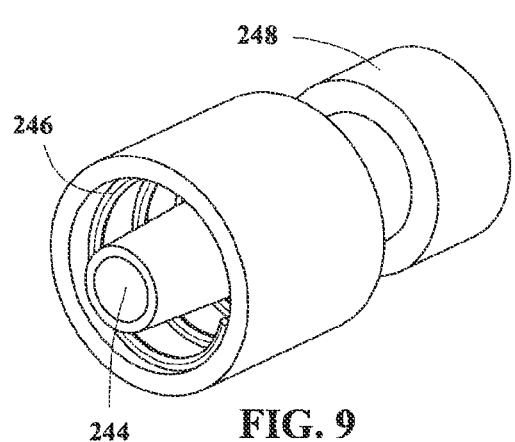
FIG. 9 is a perspective view of the catheter connector of the embodiment shown in FIG. 2.

Catheter connector 212 incorporates inner lumen 244 as shown in FIG. 9. Inner lumen 244 ensures that guide wire 216 may pass freely through catheter connector 212. Barrel segment 248 of catheter connector 212 is seated within the inner lumen of actuator rail distal end 206 as shown in FIG. 4C. Barrel segment 248 of catheter connector 212 ensures that catheter connector 212 resides securely disposed within actuator rail 204 but may rotate independent of actuator rail 204. Catheter connector 212 incorporates female threaded portion 246 that may be tightened upon the male threaded portion of the hub of an OTW catheter to securely attach guide wire incorporating a handle 200 to an OTW type catheter.

Catheter connector 212 may be formed of medical grade polycarbonate, polyvinyl chloride, acrylic, acrylonitrile butadiene styrene (ABS), nylon or other rigid biocompatible material using a molding process, a machining process or using any other processes known to those skilled in the art.

Distal and proximal guard rail bearings, 220, 222, respectively have an outer diameter of the order of 10 millimeters, an inner diameter of 5 millimeters and a thickness of 3 millimeters. Distal and proximal guard rail bearings, 220, 222, respectively ensure that guard rail 210 may rotate with a minimum of friction so that when guide wire actuator 202 slides distally or proximally upon actuator rail 204 a minimum of resistance is encountered as guide wire holding pin 214 rotates guard rail 210. In the embodiments shown in FIGS. 2 & 3 distal and proximal guard rail bearings, 220, 222, respectively, are manufactured from medical grade stainless steel by NSK Micro Precision Co. LTD, Tokyo, Japan.

In the embodiments shown in FIGS. 2, 3, 4A, 4B & 4C guard rail 210 is mounted within actuator rail 204 by means of distal and proximal guard rail bearings, 220, 222, respectively and distal and proximal guard rail connectors, 224, 226, respectively, although guard rail 210 could be mounted within actuator rail by various other means. In another embodiment guard rail 210 is mounted within actuator rail 204 without the use of bearings and in another embodiment guard rail 210 is mounted within actuator rail 204 without the use of bearings or connectors.

Figure 10A:
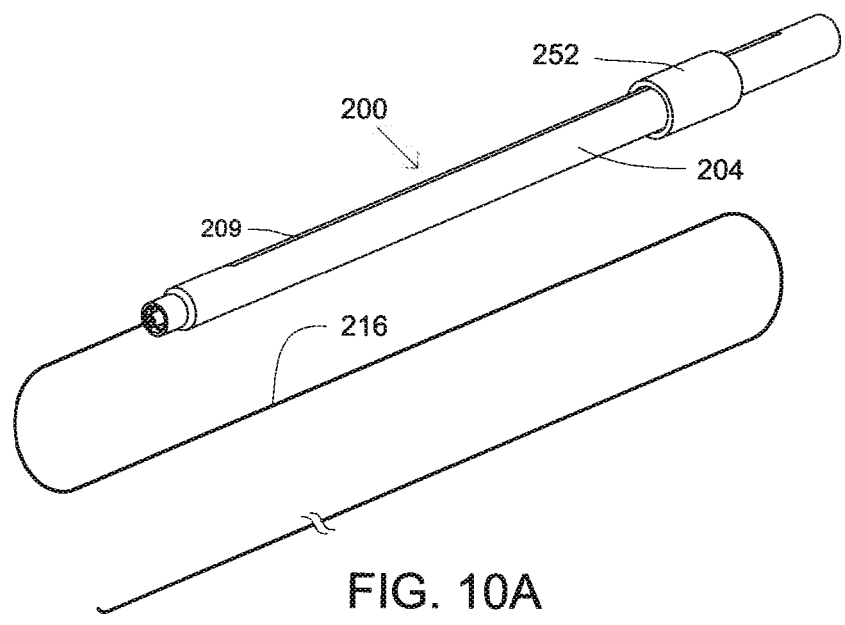
FIG. 10A is a perspective view of guide wire incorporating a handle with a modified guide wire actuator.
Figure 10B:
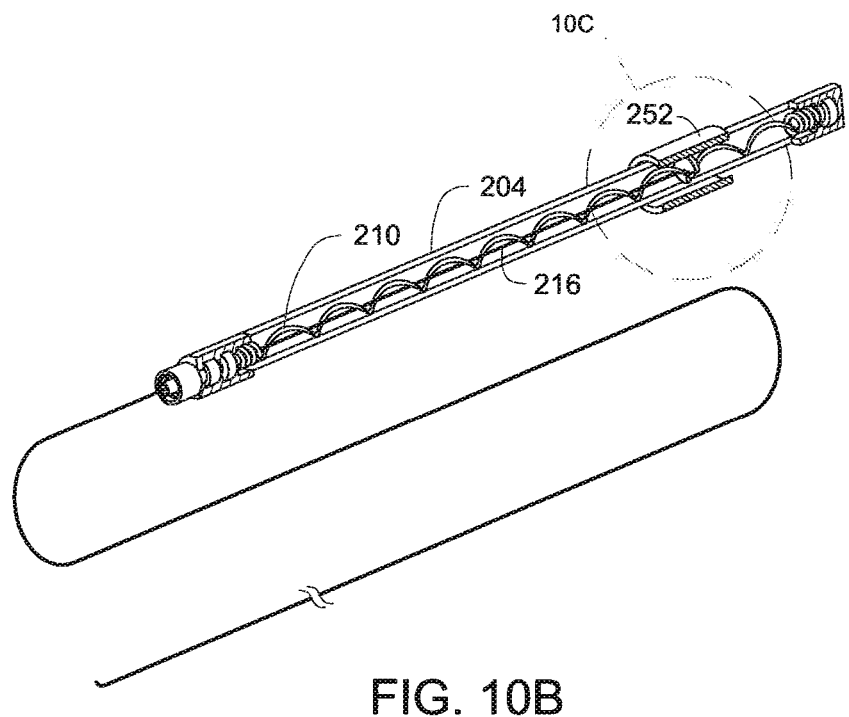
FIG. 10B is a partial sectional view of the embodiment shown in FIG. 10A.
Figure 10C:
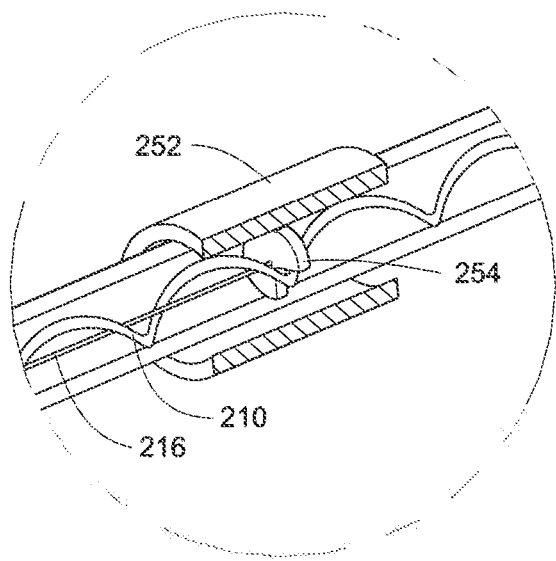
FIG. 10C is an enlarged view of the area circled and labeled 10C in FIG. 10B.
Figure 10D:
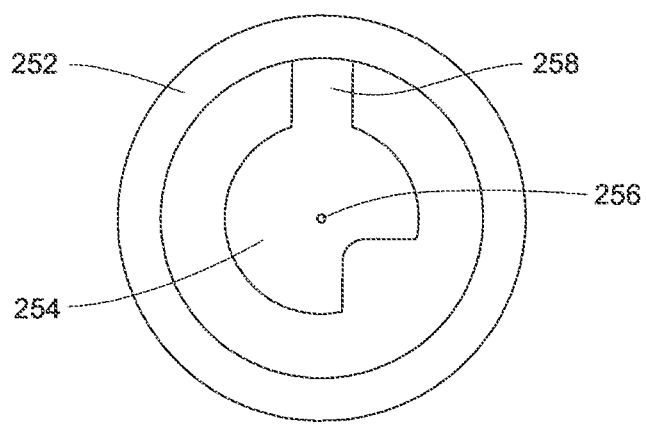
FIG. 10D is an end elevation view of the modified guide wire actuator shown in FIG. 10A, 10B, 10C.

FIG. 10A shows a perspective view of guide wire incorporating a handle 200 with modified guide wire actuator 252. FIG. 10B shows a partial perspective sectional view showing modified guide wire actuator 252 sectioned and actuator rail 204 sectioned to clearly show the inner mechanism of modified guide wire actuator 252. Modified guide wire actuator 252 consists of key element 254 that resides within inner lumen of actuator rail 204. As shown in FIG. 10D key element 254 is generally disk shaped with a large portion of one quadrant of the disk removed. Stem portion 258 of key element 254 joins the disk shaped element to the outer portion of modified guide wire actuator 252. Stem portion 258 resides within longitudinal slot 209 of actuator rail 204 and ensures that modified guide wire actuator 252 may not rotate independent of actuator rail 204. Guide wire 216 is inserted into center hole 256 of key element 254 and fixed in position using medical grade glue or other mechanical means known to those skilled in the art. Guard rail 210 resides disposed in the cut away segment of key element 254 as shown in FIG. 10C. When modified guide wire actuator 252 is advanced distally or retracted proximally, key element 254 advances or retracts and rotates guard rail 210.

Figure 11A:
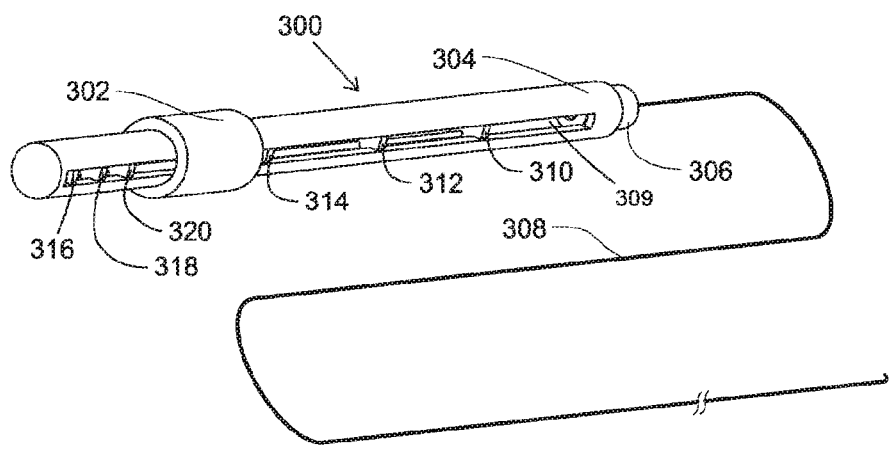
FIG. 11A is a perspective view of guide wire incorporating a handle 300 in accordance with another embodiment of the invention.
Figure 11B:
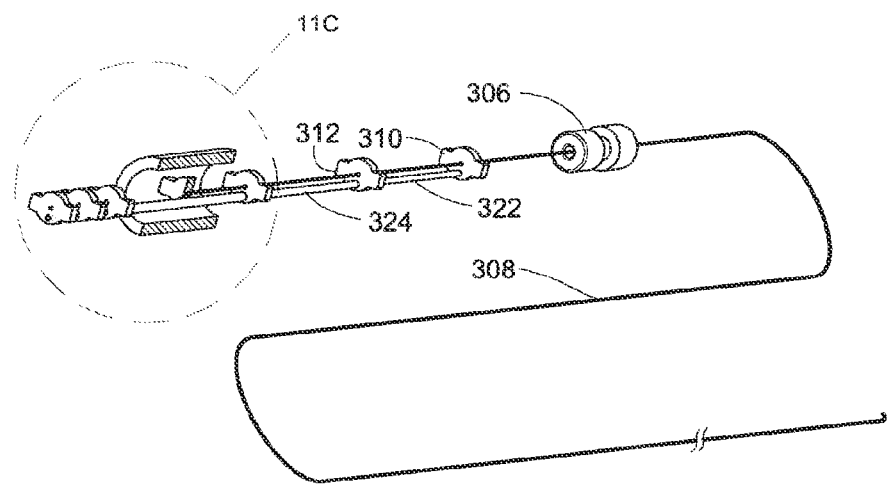
FIG. 11B shows the same perspective view of FIG. 11A with the modified guide wire actuator shown sectioned and the actuator rail omitted to clearly show the inner mechanisms that it would otherwise obscure.

FIG. 11A shows a perspective view of guide wire incorporating a handle 300 in accordance with another embodiment of the invention. FIG. 11B shows the same perspective view of FIG. 11A with guide wire actuator 302 shown sectioned and actuator rail 304 omitted to clearly show the inner mechanisms that it would otherwise obscure.

Figure 11C:
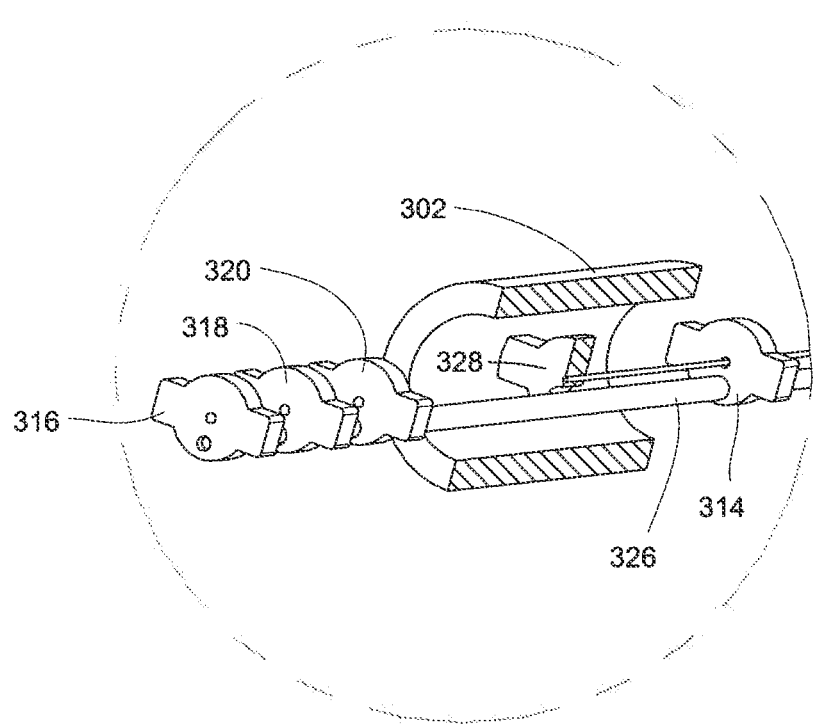
FIG. 11C is an enlarged view of the area circled and labeled 11C in FIG. 11B.
Figure 11D:
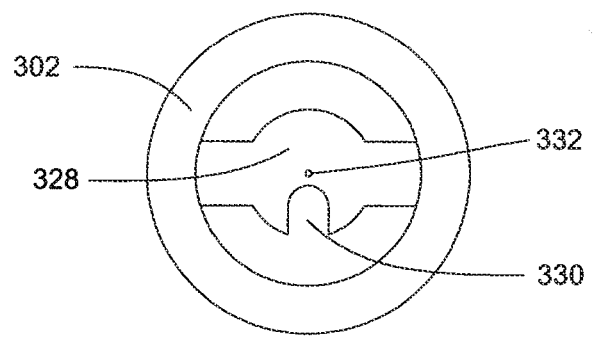
FIG. 11D is an end elevation view of the modified guide wire actuator shown in FIG. 11A.

FIG. 11C is an enlarged view of the area circled and labeled 11C in FIG. 11B. FIG. 11D is an end elevation view of guide wire actuator 302.

Guide wire actuator 302 is slidably disposed upon actuator rail 304. Guide wire actuator 302 includes fin element 328 that is securely attached to the proximal end of guide wire 308. As shown in FIG. 11D, fin element 328 consists of a circular portion that sits within the inner lumen of actuator rail 304 and winged portions that sit within longitudinal slots 309 of actuator rail 304. Notch 330 facilitates passage of hypotube 326 so that guide wire actuator 302 may slide freely relative to hypotube 326. Fin element 328 of guide wire actuator 302 ensures guide wire actuator may not rotate independent of actuator rail 304. Center hole 332 of fin element 328 facilitates secure attachment of the proximal end of guide wire 308. In the embodiment shown in FIGS. 11A, 11B, 11C the proximal end of guide wire 308 is inserted into center hole 332 of fin element 328 and securely fixed in position using uv curable glue familiar to those skilled in the art. The proximal end of guide wire 308 could alternatively be attached to fin element 328 by mechanical means including crimping, welding or other means known to those skilled in the art.

Guide wire actuator 302 may be molded from a suitable rigid plastic material such as medical grade polycarbonate, polyvinyl chloride, acrylic, acrylonitrile butadiene styrene (ABS), nylon, nylon based co-polymers or other rigid biocompatible materials, or from any suitable molding material. Alternatively guide wire actuator 302 may be made of a suitable metal material such as stainless steel or guide wire actuator 302 may comprise both metal and plastic components. Alternatively guide wire actuator 302 may be formed from machined components whereby the functionality of the machined components satisfies the functionality of the previously described molded component(s). For ease in manufacturing, guide wire actuator 302 may be comprised of molded parts that snap-fit together to form the final configuration.

Actuator rail 304 is a generally rigid tubular shaped component with an inner lumen that runs along a majority of the length of actuator rail 304 and longitudinal slots 309 on opposing sides of actuator rail 304 that run along a majority of the length of actuator rail 304. The inner surface of actuator rail 304 incorporates housings that facilitate secure disposal of catheter connector 306. Catheter connector 306 may rotate independent of actuator rail 304 but may not undergo any axial displacement.

Actuator rail 304 serves as a rail mechanism for guide wire actuator 302 enabling guide wire actuator 302 to slide in a proximal or distal direction for the length of longitudinal slots 309. Actuator rail 304 serves as the main body of guide wire incorporating a handle 300 and as a gripping member. Actuator rail 304 also serves to house the guard rail mechanism and the proximal end of guide wire 308 preventing the possibility of inadvertent bending or kinking of the proximal end of guide wire 308.

Actuator rail 304 may be molded from a suitable rigid plastic material such as nylon or nylon based co-polymers or from any suitable molding material. Alternatively actuator rail 304 may be made of a suitable metal material such as stainless steel or actuator rail 304 may comprise both metal and plastic components. Alternatively actuator rail 304 may be formed from machined components whereby the functionality of the machined components satisfies the functionality of the previously described molded component(s). For ease in manufacturing actuator rail 304 may be comprised of molded parts that snap-fit together to form the final configuration. Actuator rail 304 is generally cylinder shaped in the embodiment shown in FIG. 11A but may also incorporate any geometric configuration that enables the functionality previously described.

In the embodiment shown in FIGS. 11A, 11B, 11C, the guard rail mechanism is comprised of centering elements 310, 312, 314, 316, 318 & 320 and tubular elements 322, 324 & 326 that cooperate together to provide a system that prevents the proximal end of guide wire 308 from buckling out through longitudinal slots 309 of actuator rail 304. Centering elements 310, 312, 314, 316, 318 & 320 have a center hole through which a guide wire can freely pass. Centering elements 310, 312, 314, 316, 318 & 320 are slidably disposed within actuator rail 304 and wings on centering elements 310, 312, 314, 316, 318 & 320 sit within longitudinal slots 309 of actuator rail 304. Centering elements 310, 312 & 314 serve to prevent the proximal segment of guide wire 308 from buckling out through longitudinal slots 309 of actuator rail 304.

Centering elements, 310, 316, are securely attached to opposite ends of mandrel 322. In the embodiment shown in FIGS. 11A, 11B, mandrel 322 is a teflon coated stainless steel mandrel of sufficient circular cross section to provide sufficient rigidity to not undergo any bending or deformation during the operation and use of guide wire incorporating a handle 300. Mandrel 322 is a push fit within cylindrical holes in centering elements, 310, 316. Mandrel 322 and centering elements, 310, 316, may slide together within actuator rail 304 but may not slide independent of each other as centering elements, 310, 316, are securely fixed to mandrel 322. Centering elements, 312, 318, are securely attached to alternate ends of hypotube 324. Hypotube 324 is slidably disposed upon mandrel 322. In the embodiment shown in FIGS. 11A, 11B, 11C, hypotube 324 is a stainless steel hypotube with an internal diameter greater than the diameter of mandrel 322. Centering elements, 312, 318, and hypotube 324 form a sub assembly that may slide within longitudinal slots 309 of actuator rail 304 and also upon mandrel 322. Centering elements, 314, 320, are securely attached to alternate ends of hypotube 326. Hypotube 326 is slidably disposed upon hypotube 324. In the embodiment shown in FIGS. 11A, 11B, 11C, hypotube 326 is a stainless steel hypotube with an internal diameter greater than the outer diameter of hypotube 324. Centering elements, 314, 320, and hypotube 326 form a sub assembly that may slide within longitudinal slots 309 of actuator rail 304 and also upon hypotube 324.

When guide wire actuator is moved in a proximal direction upon actuator rail 304, fin element 328 will contact centering element 320 and displace it proximally. Centering element 320 will contact and displace centering element 318 proximally which will in turn contact and displace centering element 316 proximally. Proximal displacement of centering elements 320, 318, 316, will result in proximal displacement of the attached mandrel and hypotubes, 322, 324, 326, respectively, and centering elements, 310, 312, 314.

When guide wire actuator 302 is advanced distally from a proximal location, fin element 328 may advance freely relative to hypotube 326 and the attached centering elements, 314, 320. Notch 330 of fin element 328 facilitates passage of hypotube 326. Centering elements, 310, 312, 314, act as support points that prevent guide wire 308 from buckling as guide wire actuator 302 is advanced distally. As guide wire actuator 302 slides further distally, fin element 328 will contact centering element 314 and displace it distally. Centering element 314 will contact and displace centering element 312 distally which will in turn contact and displace centering element 310 distally. Distal displacement of centering elements 314, 312, 310, will result in distal displacement of the attached mandrel and hypotubes, 322, 324, 326, respectively, and centering elements, 316, 318, 320. The sliding motion of centering elements 310, 312, 314, 316, 318, 320 coupled with the telescopic arrangement of mandrel 322 and hypotubes, 324, 326 allows guide wire actuator 302 to slide along the full length of actuator rail 304 and to displace centering elements 310, 312, 314, 316, 318, 320 as necessary.

The arrangement of centering elements 310, 312, 314, 316, 318, 320 and mandrel 322 and hypotubes, 324, 326 ensures that centering elements 310, 312, 314 are relatively evenly spaced along the length of the segment of guide wire 308 contained within actuator rail 304. When guide wire actuator 302 is advanced and then retracted, centering elements 310, 312, 314 are repositioned along the segment of guide wire 308 contained within actuator rail 304 to their original spacing. In the embodiment shown in FIG. 11A centering elements, 310, 312, 314 provide three support points that prevent the proximal segment of guide wire 308 from buckling but additional centering elements could be included as necessary.

Figure 12A:
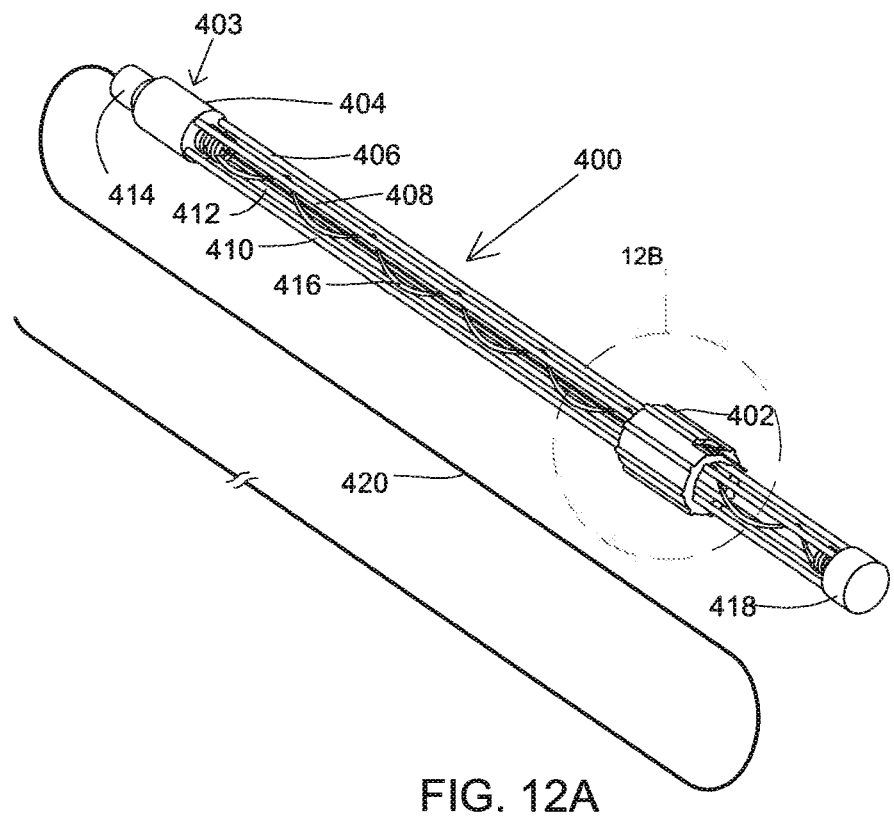
FIG. 12A shows a perspective view of guide wire incorporating a handle 400 in accordance with another embodiment of the invention.
Figure 12B:
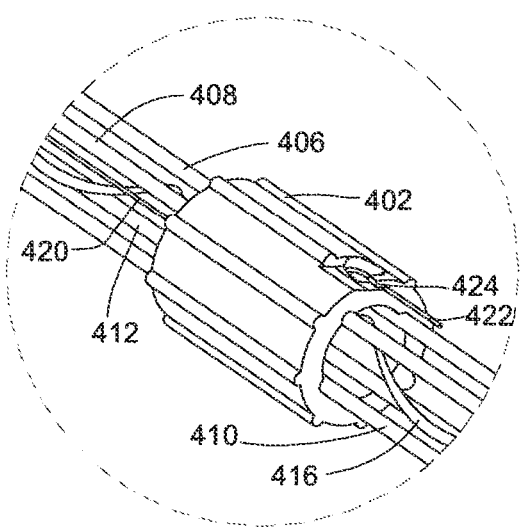
FIG. 12B is an enlarged view of the area circled and labeled 12B in FIG. 12A.
Figure 12C:
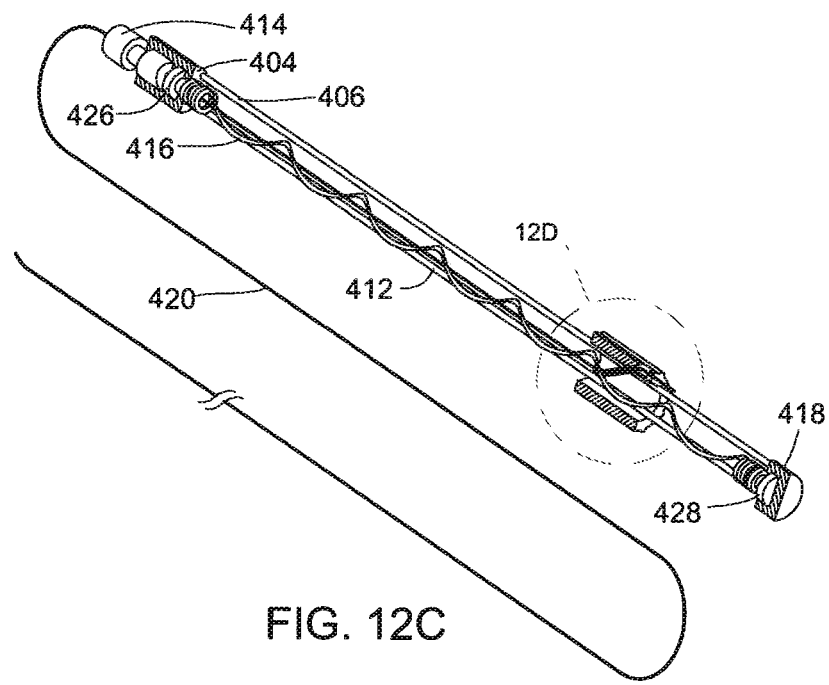
FIG. 12C is a perspective partial sectional view of the embodiment shown in FIG. 12A.

FIG. 12A shows a perspective view of guide wire incorporating a handle 400 in accordance with another embodiment of the invention. FIG. 12B is an enlarged view of the area circled and labeled 12B in FIG. 12A. FIG. 12C is a perspective partial sectional view of guide wire incorporating a handle 400. Guide wire actuator 402 and actuator rail 403 are shown sectioned in FIG. 12C to clearly show the inner mechanisms of guide wire incorporating a handle 400 that they would otherwise obscure.

In this embodiment actuator rail 403 is comprised of actuator rail distal segment 404, actuator rail proximal segment 418 and rail elements 406, 408, 410, 412. Actuator rail distal segment 404 is a generally cylindrical shaped component with an inner lumen that facilitates housing of catheter connector 414 and distal guard rail connector 426. Catheter connector 414 and distal guard rail connector 426 reside securely disposed within actuator rail distal segment 404 and may not undergo any misalignment or axial displacement relative to actuator rail distal segment 404 but may rotate independent of actuator rail distal segment 404. Catheter connector 414 incorporates an inner lumen through which guide wire 420 may freely pass. A female threaded portion of catheter connector 414 may be attached to the male threaded portion of the hub of an OTW type catheter device. Four cylindrical holes extending inward from the proximal face of actuator rail distal segment 404 facilitate secure attachment of rail elements 406, 408, 410, 412. In the embodiment shown in FIG. 12A, rail elements 406, 408, 410, 412 are a push fit within the cylindrical holes on the proximal face of actuator rail distal segment 404 although other methods of attachment could be employed including uv curable glues or other mechanical means or methods known to those skilled in the art.

Actuator rail proximal segment 418 is a generally cylindrical shaped component with an inner lumen that facilitates housing of proximal guard rail connector 428. Proximal guard rail connector 428 resides securely disposed within actuator rail proximal segment 418 and may not undergo any misalignment or axial displacement relative to actuator rail proximal segment 418 but may rotate independent of actuator rail proximal segment 418. Four cylindrical holes extending inward from the distal face of actuator rail proximal segment facilitate secure attachment of rail elements 406, 408, 410, 412. In the embodiment shown in FIG. 12A, rail elements 406, 408, 410, 412 are a push fit within the cylindrical holes on the distal face of actuator rail proximal segment 418 although other methods of attachment could be employed including uv curable glues or other mechanical means or methods known to those skilled in the art. Actuator rail distal segment 404 and actuator rail proximal segment 418 may be formed of medical grade polycarbonate, polyvinyl chloride, acrylic, acrylonitrile butadiene styrene (ABS), nylon or other rigid biocompatible material using a molding process, a machining process or using any other processes known to those skilled in the art.

Rail elements 406, 408, 410, 412 may be formed from stainless steel rod with a circular cross section of sufficient diameter to provide sufficient rigidity so that rail elements 406, 408, 410, 412 do not undergo any bending or twisting during operation of guide wire incorporating a handle 400.

Figure 12D:
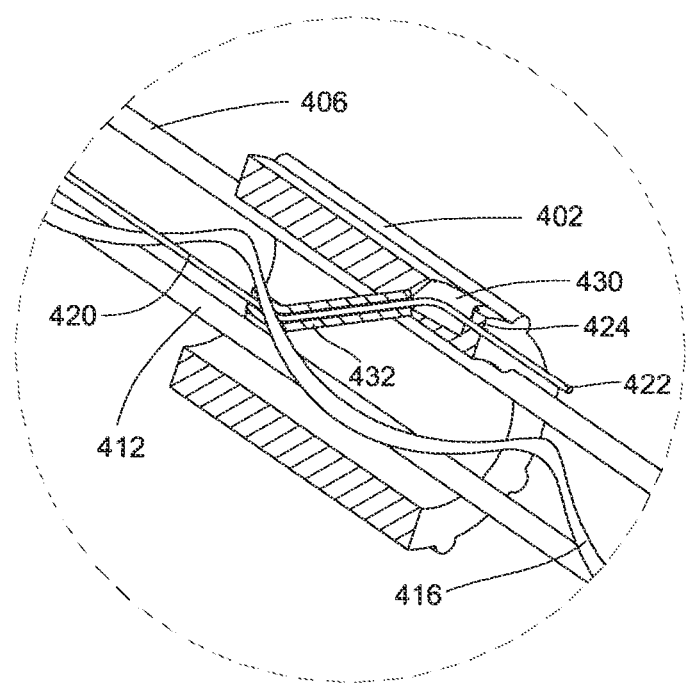
FIG. 12D is an enlarged view of the area circled and labeled 12D in FIG. 12C.
Figure 13:
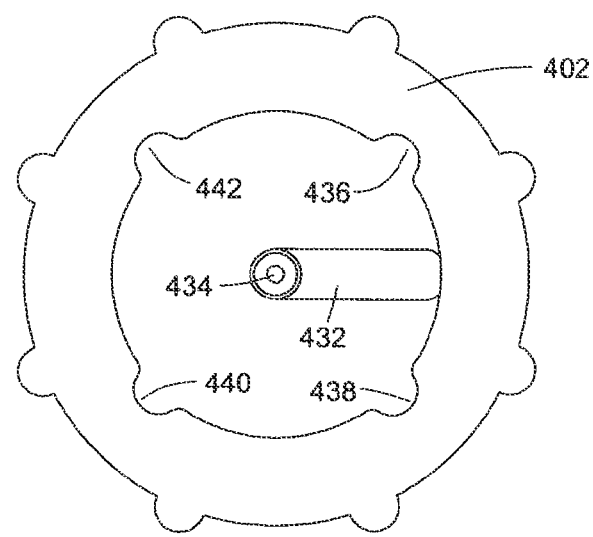
FIG. 13 is an end elevation view of the guide wire actuator shown in FIG. 12A.

FIG. 13 shows an end elevation view of guide wire actuator 402. The inner surface of guide wire actuator 402 incorporates channels 436, 438, 440 & 442 that seat upon rail elements 406, 408, 410, 412. Guide wire actuator 402 may slide along rail elements 406, 408, 410 & 412. Rotation of guide wire actuator 402 will result in rotation of actuator rail 403. FIG. 12D shows an enlarged sectional view of the area circled and labeled 12D in FIG. 12C. Guide wire actuator 402 incorporates tube segment 432 that continues on from the apex of conical cavity 430 inclined at an angle to the longitudinal axis of guard rail 416. Tube segment 432 incorporates a bend at its distal end so that guide wire 420 is aligned with longitudinal axis of guard rail 416 as it exits from inner lumen 434 of the distal end of tube segment 432, as shown in FIG. 13.

Referring to FIGS. 12B, 12D, guide wire proximal end 422 is held in place by locking clip 424 of guide wire actuator 402. Locking clip 424 incorporates a tapered slot that facilitates insertion of guide wire proximal end 422 and secure attachment by forcing guide wire proximal end 422 further into the tapered slot of locking clip 424. Sliding guide wire proximal end 422 out of the tapered slot of locking clip 424 releases guide wire proximal end 422 from its attachment to guide wire actuator 402 so that guide wire 420 may be retracted from guide wire incorporating a handle 400. Conical cavity 430 facilitates loading of the tip of guide wire 420 into tube segment 432. Insertion of the tip of guide wire 420 into conical cavity 430 guides the tip of the guide wire to the apex of conical cavity 430 where the inner lumen of tube segment 432 is aligned so that the tip of guide wire 420 advances through tube segment 432. When guide wire actuator 402 is advanced distally tube segment 432 contacts and rotates guard rail 416 so that tube segment 432 can remain in communication with inner lumen of guard rail 416 along its length.

Guide wire actuator 402 may be molded from a suitable rigid plastic material such as medical grade polycarbonate, polyvinyl chloride, acrylic, acrylonitrile butadiene styrene (ABS), nylon, nylon based co-polymers or other rigid biocompatible materials, or from any suitable molding material. In the embodiment shown in FIGS. 12A, 12B, 12C & 12D tube segment 432 is insert molded as part of the molding of the main cylindrical segment of guide wire actuator 402. Alternatively guide wire actuator 402 may be made of a suitable metal material such as stainless steel or guide wire actuator 402 may comprise both metal and plastic components. Alternatively guide wire actuator 402 may be formed from machined components whereby the functionality of the machined components satisfies the functionality of the previously described molded component(s). For ease in manufacturing guide wire actuator 402 may be comprised of molded parts that snap-fit together to form the final configuration.

Figure 14:
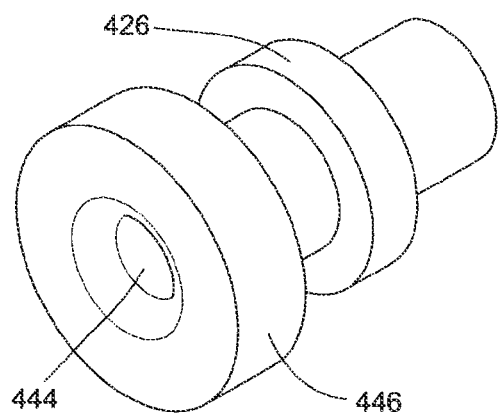
FIG. 14 is a perspective view of the distal guard rail connector of the embodiment shown in FIG. 12C.

Guard rail 416 is a generally rigid structure formed from wire material wound about a longitudinal axis into a helix type formation. The ends of guard rail 416 are so formed to form a cylindrical type lumen that seats onto distal and proximal guard rail connectors, 426, 428, respectively. FIG. 14 shows a perspective view of distal guard rail connector 426. Distal guard rail connector 426 has a central lumen 444 through which guide wire 420 may freely pass. Advancing of guide wire actuator 402 distally results in the distal end of tube segment 432 seating within central lumen 444 of distal guard rail connector 426. Disk segment 446 of distal guard rail connector 426 seats within housing on the inside of actuator rail 403 and aligns distal guard rail connector 426 within actuator rail 403. Distal guard rail connector 426 is a push fit into the inner lumen of guard rail 416.

Figure 15:
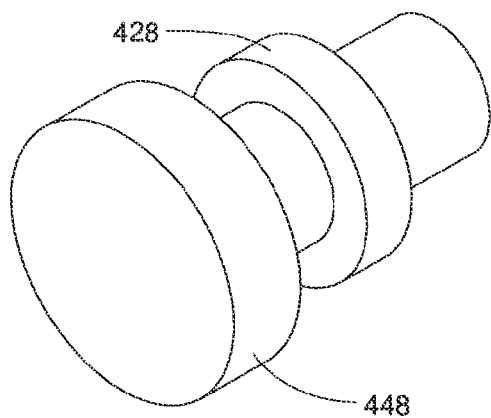
FIG. 15 is a perspective view of the proximal guard rail connector of the embodiment shown in FIG. 12C.

FIG. 15 shows a perspective view of proximal guard rail connector 428. Disk segment 448 of proximal guard rail connector 428 seats within housing of actuator rail 403 and aligns proximal guard rail connector 428 with actuator rail 403. Proximal guard rail connector 428 is a push fit into the inner lumen of guard rail 416.

Distal and proximal guard rail connectors, 426, 428, respectively and catheter connector 414 may be formed of medical grade polycarbonate, polyvinyl chloride, acrylic, acrylonitrile butadiene styrene (ABS), nylon or other rigid biocompatible material. Distal and proximal guard rail connectors, 426, 428, respectively and catheter connector 414 may be formed using a molding process or may be machined using other processes known to those skilled in the art.

In the embodiment shown in FIG. 12A, guide wire 420 may be disengaged and removed from guide wire incorporating a handle 400. Referring to FIG. 12B, guide wire proximal end 422 can be pushed sideways out of the tapered notch of locking clip 424 and then retracted out of tube segment 432. Tube segment 432 is designed so that it does not permanently deform the shape of guide wire 420 passing through the curved segment. Removed guide wire 420 can be reinserted into guide wire incorporating a handle 400 when guide wire actuator 402 slides fully distally so that tube segment 432 is nested within central lumen 444 of distal guard rail connector 426. Insertion of the tip of guide wire 420 into conical cavity 430 guides the tip into tube segment 432. Further advancing guide wire 420 will advance the tip of guide wire 420 through tube segment 432 into central lumen 444 of distal guard rail connector and through the inner lumen of catheter connector 414. Guide wire incorporating a handle 400 may be used in conjunction with guide wire 420 or alternatively any suitably sized guide wire could be used with guide wire incorporating a handle 400. Guide wire incorporating a handle 400 allows for the removal of guide wire 420 and reinsertion if desired or the insertion of an alternate guide wire if guide wire 420 were to become damaged for example.

Figure 16A:
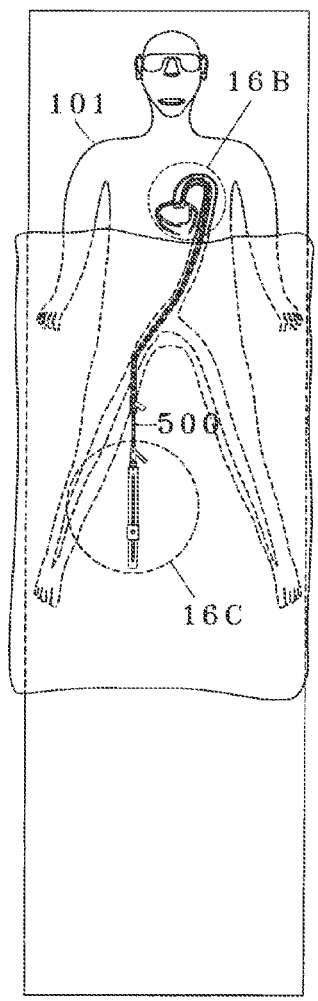
FIG. 16A is an illustration of a guide wire incorporating a handle conjoined with an OTW catheter system inserted into an in-dwelling guide catheter in a patient during an interventional procedure.
Figure 16B:
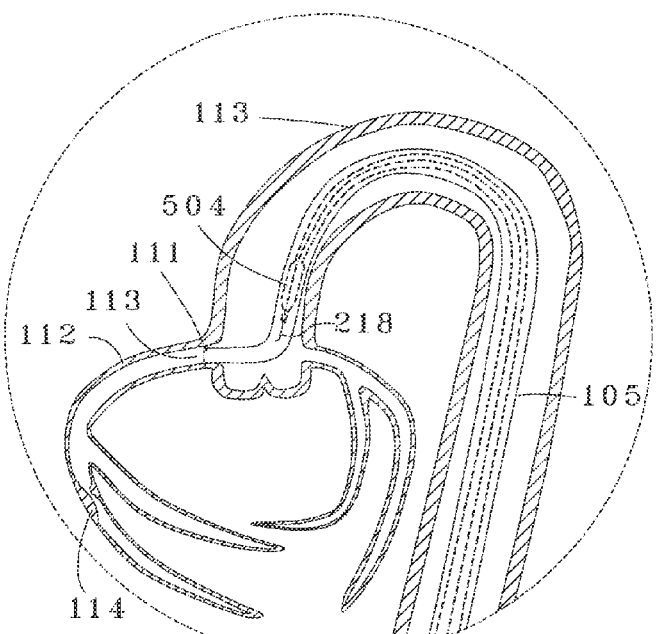
FIG. 16B is an enlarged sectional view of the area circled and labeled 16B in FIG. 16A.
Figure 16C:
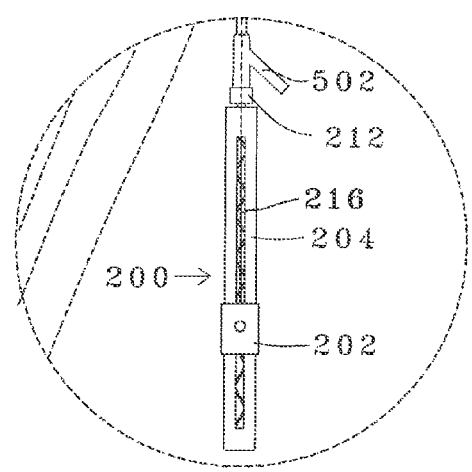
FIG. 16C is an enlarged view of the area circled and labeled 16C in FIG. 16A.

The operation and use of guide wire incorporating a handle 200 will now be described by explaining its use during a coronary angioplasty procedure. Guide wire incorporating a handle 200 has been attached to OTW catheter 500 as shown in FIG. 5A. Guide wire actuator 202 is positioned near actuator rail proximal end 208 so that a short segment of guide wire 216 is protruding distally from the distal end of OTW catheter 500. This short segment may be of the order of 1 inch in length and guide wire distal end 218 may be shaped by the clinician to aid in navigating the vasculature. Actuator rail 204 may be used as a gripping mechanism to navigate the conjoined devices through the main lumen of an in-dwelling guide catheter and within the vasculature of a patient. FIGS. 16A, 16B, 16C illustrate conjoined guide wire incorporating a handle 200 and OTW catheter 500 advanced to the distal end of guide catheter 105 pre-positioned within ostium 113 of coronary vessel 112 of patient 101. Guide wire incorporating a handle 200 and OTW catheter 500 have been advanced simultaneously through the main lumen of guide catheter 105 without the requirement to maintain independent control over both guide wire 216 and OTW catheter 500. Distal end of OTW catheter 500 is enveloped within the lumen of guide catheter 105 so that OTW catheter 500 is not in direct contact with coronary vessel 112. In the illustration shown in FIG. 16B balloon of OTW catheter 504 and guide wire distal end 218 are positioned within the lumen of guide catheter 105 proximal to guide catheter tip 111.

Guide wire actuator 202 may be advanced distally upon actuator rail 204 while holding hub of OTW catheter 502 stationary to advance guide wire distal end 218 past stenosis 114 within coronary vessel 112. Guide wire actuator 202 may be used to advance guide wire 216 within coronary vessel 112 with one sliding motion of guide wire actuator 202 along actuator rail 204 as opposed to a series of short incremental pushes as previously described in the background of the invention. Guide wire actuator 202 may be rotated while holding hub of OTW catheter 502 stationary to rotate actuator rail 204 independent of OTW catheter 500, and subsequently rotate guide wire 216 independent of OTW catheter 500 to assist in navigating guide wire distal end 218 to the desired location. When guide wire 216 is positioned at treatment site within coronary vessel 112, hub of catheter 502 may be advanced while maintaining position of guide wire actuator 202 stationary to advance OTW catheter 500 to the treatment site while maintaining guide wire 216 stationary. After treatment with OTW catheter 500, guide wire incorporating a handle 200 and OTW catheter 500 may be removed from vasculature simultaneously by retracting actuator rail 204. Alternatively guide wire incorporating a handle 200 can be detached from OTW catheter 500 by unscrewing catheter connector 212 from hub of OTW catheter 502 and guide wire incorporating a handle 200 may then be removed from the patient's vasculature while leaving OTW catheter 500 in place to enable a guide wire exchange, if required.

Guide wire incorporating a handle 200 may be used for procedures in areas including but not limited to interventional cardiology, interventional radiology, interventional bronchospy, gastroenterology and urology that utilize a guide wire and a catheter based device.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A guide wire operating system comprising:
(a) an actuator rail having an inner lumen along at least a majority of a length of the actuator rail for accepting a guide wire, a longitudinal opening along a majority of a length of said actuator rail, said actuator rail being adapted to be connected to an associated catheter device in a manner such that said actuator rail is rotatable relative to a connected catheter;
(b) a guide wire operating mechanism including a guide wire actuator adapted to be connected to a proximal end portion of a guide wire in the inner lumen of said actuator rail and slidably operable along a full length of said longitudinal opening;
(c) a guard rail contained entirely within said actuator rail and comprising a member extending continuously for at least the full length of said longitudinal opening, said guard rail being independent of and not connected to, but configured to confine said guide wire along the length of said longitudinal opening in said inner lumen of said actuator rail while enabling said guide wire actuator to slide freely along the full length of said longitudinal opening while connected to said guide wire; and
(d) wherein said guide wire operating system is configured to enable simultaneous and independent operation of said guide wire and a catheter device connected to said actuator rail while also enabling independent rotation of said guide wire relative to an associated catheter device.

2. A guide wire operating system as in claim 1 wherein said actuator rail further comprises a catheter connector that enables connection to a hub of a catheter device, said catheter connector being rotatable relative to said actuator rail.

3. A guide wire operating system as in claim 1 wherein said guard rail is a generally rigid wound wire structure.

4. A guide wire operating system as in claim 3 Wherein the helically-shaped component of said guard rail has a pitch to diameter ratio such that said guide wire actuator causes said helically-shaped component to rotate as it travels alongside.

5. A guide wire operating system as in claim 1 wherein said actuator rail comprises a plurality of longitudinal slots.

6. A guide wire operating system as in claim 1 further comprising a wire fixing arrangement for fixing the proximal portion of an inserted guide wire relative to said guide wire actuator.

7. A guide wire operating system as in claim 6 wherein said wire fixing arrangement comprises a locking clip.

8. A guide wire operating system as in claim 7 wherein said guide wire actuator comprises a tube element that co-operates with said locking clip.

9. A guide wire operating system as in claim 1 including a device to prevent rotation of said guide wire actuator with respect to said actuator rail.

10. A guide wire operating system as in claim 1 wherein said guard rail comprises an elongate mandrel, a plurality of centering elements through which a guide wire can pass, spaced along the length of said actuator rail, fixed to and operated in conjunction with said mandrel and telescoping hypotubes in slidable relation within said actuator rail in a manner that maintains the shape of a guide wire within said actuator rail during sliding of said guide wire actuator.

11. A guide wire operating system as in claim 1 wherein said actuator rail is a rigid tubular member.

12. A guide wire operating system as in claim 1 further comprising a guide wire fixed to said guide wire actuator.

13. A guide wire operating system as in claim 1 wherein said catheter system is an over-the-wire (OTW) catheter device.

14. A guide wire operating system as in claim 1 wherein said guard rail arrangement comprises a rigid elongate helically-shaped member that winds about an installed guide wire for at least the full length of said longitudinal opening, said guard rail being rotatable relative to said guide wire and configured to be rotated by said guide wire actuator as said guide wire actuator is operated along said longitudinal opening.

15. A guide wire operating system as in claim 14 wherein said guard rail further comprises bearings and connectors to facilitate low friction rotation of said rigid elongate helically-shaped member.

16. A guide wire operating system as in claim 1 wherein said actuator rail comprises a distal segment and a proximal segment joined by a plurality of spaced radially distributed elongated rod elements.

17. A catheter system comprising:
(a) a guide wire operating system further comprising:
  (1) an actuator rail having an inner lumen along at least a majority of a length of the actuator rail for accepting a guide wire, a longitudinal opening along a majority of the length of said actuator rail, said actuator rail being adapted to be connected to an associated catheter device in a manner such that said actuator rail is rotatable relative to a connected catheter;
  (2) a guide wire operating mechanism including a guide wire actuator adapted to be connected to a proximal end portion of a guide wire in the inner lumen of said actuator rail and slidably operable along the full length of said longitudinal opening;
  (3) a guard rail contained entirely within said actuator rail and comprising a member extending continuously for at least a full length of said longitudinal opening, said guard rail being independent of and not connected to but configured to confine said guide wire along the length of said longitudinal opening in said inner lumen of said actuator rail while enabling said guide wire actuator to slide freely along the full length of said longitudinal opening while connected to said guide wire; and
(b) a catheter device connected to said actuator rail; and
(c) wherein said guide wire operating system is configured to enable simultaneous and independent operation of said guide wire and said catheter device connected to said actuator rail while also enabling independent rotation of said guide wire relative to said catheter device.

18. A catheter system as in claim 17 wherein said actuator rail further comprises a catheter connector that enables connection to a hub of a catheter device, said catheter connector being rotatable relative to said actuator rail.

19. A catheter system as in claim 17 wherein said catheter device is an over-the-wire (OTW) catheter device.

20. A method of operating a guide wire system comprising:
(a) providing a guide wire operating system comprising:
  (1) an actuator rail having an inner lumen along at least a majority of a length of the actuator rail for accepting a guide wire, a longitudinal opening along a majority of the length of said actuator rail, said actuator rail being adapted to be connected to an associated catheter device in a manner such that said actuator rail is rotatable relative to a connected catheter;
  (2) a guide wire operating mechanism including a guide wire actuator adapted to be connected to a proximal end portion of a guide wire in the inner lumen of said actuator rail and slidably operable along a full length of said longitudinal opening;
  (3) a guard rail contained entirely within said actuator rail and comprising a member extending continuously for at least the full length of said longitudinal opening, said guard rail being independent of and not connected to but configured to confine said guide wire along the length of said longitudinal opening in said inner lumen of said actuator rail while enabling said guide wire actuator to slide freely along the full length of said longitudinal opening while connected to a guide wire;
(b) connecting a catheter system to said actuator rail;
(c) manipulating said guide wire by moving said guide wire actuator along said longitudinal opening; and
(d) manipulating said catheter system optionally independent of or with said guide wire.

21. A method as in claim 20 wherein said catheter is an over-the-wire (OTW) device.

* * * * *